US008380536B2

(12) United States Patent
Howard et al.

(10) Patent No.: US 8,380,536 B2
(45) Date of Patent: *Feb. 19, 2013

(54) SYSTEM FOR MAINTAINING DRUG INFORMATION AND COMMUNICATING WITH MEDICATION DELIVERY DEVICES

(75) Inventors: Gary A. Howard, San Diego, CA (US); Fred Assadi, San Jose, CA (US); Yu Xin, San Diego, CA (US); Nick Okasinski, Hillsborough, CA (US); Thomas Canup, San Jose, CA (US); Steve Engebretsen, Corralitos, CA (US); Raymond P. Silkaitis, Lake Forest, IL (US); Geoffrey N. Holland, Wadsworth, IL (US); Patrick B. Keely, Grayslake, IL (US); Mozammil H. Awan, Morgan Hill, CA (US)

(73) Assignee: Hospira, Inc., Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/301,493

(22) Filed: Nov. 21, 2011

(65) Prior Publication Data

US 2012/0065990 A1    Mar. 15, 2012

Related U.S. Application Data

(63) Continuation of application No. 10/783,877, filed on Feb. 20, 2004, now Pat. No. 8,065,161.

(51) Int. Cl.
*G06Q 10/00* (2006.01)
*G06Q 50/00* (2006.01)

(52) U.S. Cl. ................. 705/2; 705/3; 604/131
(58) Field of Classification Search ............ 705/2–3; 600/300; 604/131
See application file for complete search history.

(56) References Cited

U.S. PATENT DOCUMENTS

| 4,696,671 | A | 9/1987 | Epstein et al. |
| 4,731,051 | A | 3/1988 | Fishchell |
| 4,785,969 | A | 11/1988 | McLaughlin |
| 4,908,017 | A | 3/1990 | Howson et al. |
| 4,978,335 | A | 12/1990 | Arthur, III |
| 5,058,161 | A | 10/1991 | Weiss |
| 5,088,981 | A | 2/1992 | Howson et al. |

(Continued)

FOREIGN PATENT DOCUMENTS

| DE | 199 32 147 A1 | 1/2001 |
| EP | 0 683 465 A2 | 11/1995 |

(Continued)

OTHER PUBLICATIONS

Bektas F., et al, Bluetooth Commun. Employing Antenna Diversity, Computers & Communication, 2003 8th IEEE Int'l Symposium Piscataway, NJ, pp. 652-657, USA.

*Primary Examiner* — Luke Gilligan
(74) *Attorney, Agent, or Firm* — Michael R. Crabb

(57) ABSTRACT

A system for maintaining drug information and communicating with medication delivery devices includes software designed for use in a hospital, pharmacy or biomedical technical service environments. The software may be provided on a computer readable medium. The software allows a facility to customize a drug library with both hard and soft drug limits and other parameters for use with an infuser having a plug and play module removably inserted into a slot within a housing, or for use with an infuser having a connectivity engine enclosed within the housing. The system supports data transfer to one or more infusers connected to one or more computers. The connection between the computer and the pump can be hard wired or wireless.

6 Claims, 39 Drawing Sheets

U.S. PATENT DOCUMENTS

| | | | |
|---|---|---|---|
| 5,097,505 A | 3/1992 | Weiss | |
| 5,100,380 A | 3/1992 | Epstein et al. | |
| 5,153,827 A | 10/1992 | Coutre et al. | |
| 5,161,222 A | 11/1992 | Montejo et al. | |
| 5,317,506 A | 5/1994 | Coutre et al. | |
| 5,319,363 A | 6/1994 | Welch et al. | |
| 5,338,157 A | 8/1994 | Blomquist | |
| 5,341,476 A | 8/1994 | Lowell | |
| 5,378,231 A | 1/1995 | Johnson et al. | |
| 5,417,222 A | 5/1995 | Dempsey et al. | |
| 5,445,621 A | 8/1995 | Poli et al. | |
| 5,455,851 A | 10/1995 | Chaco et al. | |
| 5,465,082 A | 11/1995 | Chaco | |
| 5,485,408 A | 1/1996 | Blomquist | |
| 5,507,288 A | 4/1996 | Bocker et al. | |
| 5,522,798 A | 6/1996 | Johnson et al. | |
| 5,547,470 A | 8/1996 | Johnson et al. | |
| 5,594,786 A | 1/1997 | Chaco et al. | |
| 5,620,608 A | 4/1997 | Rosa et al. | |
| 5,630,710 A | 5/1997 | Tune et al. | |
| 5,643,212 A | 7/1997 | Coutre et al. | |
| 5,658,250 A | 8/1997 | Blomquist et al. | |
| 5,669,877 A | 9/1997 | Blomquist | |
| 5,681,285 A * | 10/1997 | Ford et al. | 604/151 |
| 5,689,229 A | 11/1997 | Chaco et al. | |
| 5,699,509 A | 12/1997 | Gary et al. | |
| 5,713,856 A | 2/1998 | Eggers et al. | |
| 5,778,256 A | 7/1998 | Darbee | |
| 5,781,442 A | 7/1998 | Engleson et al. | |
| 5,788,669 A | 8/1998 | Peterson | |
| 5,814,015 A | 9/1998 | Gargano et al. | |
| 5,827,179 A | 10/1998 | Lichter et al. | |
| 5,832,448 A | 11/1998 | Brown | |
| 5,836,910 A | 11/1998 | Duffy et al. | |
| 5,850,344 A | 12/1998 | Conkright | |
| 5,867,821 A | 2/1999 | Ballantyne et al. | |
| 5,871,465 A | 2/1999 | Vasko | |
| 5,897,493 A | 4/1999 | Brown | |
| 5,915,240 A | 6/1999 | Karpf | |
| 5,924,074 A | 7/1999 | Evans | |
| 5,935,099 A | 8/1999 | Peterson et al. | |
| 5,971,594 A | 10/1999 | Sahai et al. | |
| 5,975,081 A | 11/1999 | Hood et al. | |
| 5,990,838 A | 11/1999 | Burns et al. | |
| 5,997,476 A | 12/1999 | Brown | |
| 6,003,006 A | 12/1999 | Colella et al. | |
| 6,012,034 A | 1/2000 | Hamparian et al. | |
| 6,021,392 A | 2/2000 | Lester et al. | |
| 6,024,539 A | 2/2000 | Blomquist | |
| 6,032,676 A | 3/2000 | Moore | |
| 6,073,106 A | 6/2000 | Rozen et al. | |
| 6,104,295 A | 8/2000 | Gaisser et al. | |
| RE36,871 E | 9/2000 | Epstein et al. | |
| 6,150,942 A | 11/2000 | O'Brien | |
| 6,157,914 A | 12/2000 | Seto et al. | |
| 6,159,147 A | 12/2000 | Lichter et al. | |
| 6,182,667 B1 | 2/2001 | Hanks et al. | |
| 6,189,105 B1 | 2/2001 | Lopes | |
| 6,195,589 B1 | 2/2001 | Ketcham | |
| 6,234,176 B1 | 5/2001 | Domae et al. | |
| 6,241,704 B1 | 6/2001 | Peterson et al. | |
| 6,248,067 B1 | 6/2001 | Causey, III et al. | |
| 6,259,355 B1 | 7/2001 | Chaco et al. | |
| 6,269,340 B1 | 7/2001 | Ford et al. | |
| 6,270,455 B1 | 8/2001 | Brown | |
| 6,277,072 B1 | 8/2001 | Bardy | |
| 6,280,380 B1 | 8/2001 | Bardy | |
| 6,283,761 B1 | 9/2001 | Joao | |
| 6,312,378 B1 | 11/2001 | Bardy | |
| 6,482,158 B2 | 11/2002 | Mault | |
| 6,485,418 B2 | 11/2002 | Yasushi et al. | |
| 6,494,694 B2 | 12/2002 | Lawless et al. | |
| 6,494,831 B1 | 12/2002 | Koritzinsky | |
| 6,497,680 B1 | 12/2002 | Holst et al. | |
| 6,519,569 B1 | 2/2003 | White et al. | |
| 6,544,228 B1 | 4/2003 | Heitmeier | |
| 6,581,117 B1 | 6/2003 | Klein et al. | |
| 6,589,229 B1 | 7/2003 | Connelly et al. | |
| 6,602,191 B2 | 8/2003 | Quy | |
| 6,640,246 B1 | 10/2003 | Gary, Jr. et al. | |
| 6,641,533 B2 | 11/2003 | Causey, III et al. | |
| 6,652,455 B1 | 11/2003 | Kocher | |
| 6,659,947 B1 | 12/2003 | Carter et al. | |
| 6,725,200 B1 | 4/2004 | Rost | |
| 6,752,787 B1 | 6/2004 | Causey, III et al. | |
| 6,790,198 B1 | 9/2004 | White et al. | |
| 6,809,653 B1 | 10/2004 | Mann et al. | |
| 7,256,888 B2 * | 8/2007 | Staehr et al. | 356/319 |
| 7,636,718 B1 | 12/2009 | Steen et al. | |
| 2001/0016056 A1 | 8/2001 | Westphal et al. | |
| 2001/0032099 A1 | 10/2001 | Joao | |
| 2001/0037060 A1 | 11/2001 | Thompson et al. | |
| 2001/0044731 A1 | 11/2001 | Coffman et al. | |
| 2002/0032583 A1 | 3/2002 | Joao | |
| 2002/0038392 A1 | 3/2002 | De La Huerga | |
| 2002/0169636 A1 | 11/2002 | Eggers et al. | |
| 2003/0139701 A1 | 7/2003 | White et al. | |
| 2003/0140928 A1 | 7/2003 | Bui et al. | |
| 2003/0200116 A1 | 10/2003 | Forrester | |
| 2004/0189708 A1 * | 9/2004 | Larcheveque et al. | 345/780 |
| 2005/0137573 A1 | 6/2005 | McLaughlin | |
| 2006/0100907 A1 | 5/2006 | Holland et al. | |

FOREIGN PATENT DOCUMENTS

| | | | |
|---|---|---|---|
| EP | 0 880 936 A2 | 2/1998 | |
| EP | 1157711 A2 | 11/2001 | |
| EP | 1 197 178 A1 | 4/2002 | |
| FR | 2 717 919 A1 | 9/1995 | |
| WO | 9608755 A1 | 3/1996 | |
| WO | 9812670 A1 | 3/1998 | |
| WO | 9819263 A1 | 5/1998 | |
| WO | 9951003 A2 | 10/1999 | |
| WO | 0114974 A2 | 3/2001 | |
| WO | 0133484 A2 | 5/2001 | |
| WO | 0145014 A1 | 6/2001 | |
| WO | 0236044 A2 | 5/2002 | |
| WO | 0249153 A1 | 6/2002 | |
| WO | 02081015 A1 | 10/2002 | |
| WO | 03050917 A1 | 6/2003 | |

* cited by examiner

FIG. 6

| Infuser Library Version | Infuser Serial # | CCA Name | Event Type | Alert Time | Channel And Step # | Drug Name | Drug Cont | Limit Violated | Limit Value | Limit Dosing Unit | Attempted Dose | Override ? | Program Confirmed | Intended Dose | Status |
|---|---|---|---|---|---|---|---|---|---|---|---|---|---|---|---|
| 10/06/03 1.00R-D32730 1-1005 | 13139876 | CCA 3 | Override | 10/06/03 16:10:05 | A-1 | Drug A | 1000 mcg /100 mL | Upper | 90.0 | mcg / kg / hr | 100 | Yes | Yes | 100 | Complete |
| 10/06/03 1.00R-D32730 1-1005 | 13139876 | CCA 3 | Override | 10/06/03 16:27:28 | A-1 | Drug B | 100 grams / 1000 mL | Upper | 100 | mL / hr | 101 | Yes | Yes | 101 | Complete |

FIG. 7

| COLUMN NAME | DESCRIPTION | EXAMPLE |
| --- | --- | --- |
| INFUSER LIBRARY VERSION | THE DRUG LIBRARY NAME AS IT IS STORED IN THE INFUSER. | 10/06/03 1.00R-0327301-1005 |
| INFUSER SERIAL NUMBER | THE INFUSER SERIAL NUMBER. | 13139876 |
| CCA NAME | THE CCA NAME. | CCA 3 |
| EVENT TYPE | THE TYPE OF OVERRIDE: SOFT LIMIT ALERT OR SOFT LIMIT OVERRIDE. A SOFT LIMIT ALERT IS AN OVERRIDE THAT WAS CANCELLED. A SOFT LIMIT OVERRIDE IS AN OVERRIDE THAT WAS ACCEPTED. | OVERRIDE |
| ALERT TIME | THE DATE AND TIME THE ALERT OR OVERRIDE OCCURRED. | 10/6/2003 16:29 |
| CHANNEL AND STEP NUMBER | THE CHANNEL (LINE A OR LINE B) AND STEP NUMBER OF THE THERAPY IN WHICH THE OVERRIDE OR ALERT OCCURRED. | B - 1 |
| DRUG NAME | THE NAME OF THE DRUG. | DRUG C |
| DRUG CONCENTRATION | THE DRUG CONCENTRATION. | 50 mg/100 mL |
| LIMIT VIOLATED | THE SOFT LIMIT TYPE THAT WAS OVERRIDDEN: UPPER OR LOWER. | LOWER |
| LIMIT VALUE | THE UPPER OR LOWER SOFT LIMIT VALUE IN THE DRUG ENTRY'S RULE SET. | 10 |
| LIMIT DOSING UNIT | THE DRUG DOSING UNIT. | mg/hr |
| ATTEMPTED DOSE | THE RATE VALUE ENTERED THAT VIOLATES A RULE SET. | 9 |
| OVERRIDE? | THE USER'S RESPONSE TO THE FIRST CONFIRMATION SCREEN WHEN PROGRAMMING A RATE THAT WOULD VIOLATE A RULE SET. | YES |
| PROGRAM CONFIRMATION | THE USER'S RESPONSE TO THE SECOND CONFIRMATION SCREEN WHEN PROGRAMMING A RATE THAT WOULD VIOLATE A RULE SET. | YES |
| INTENDED DOSE | THE DOSE THAT WAS PROGRAMMED AND DELIVERED. | 9 |
| STATUS | THE COMPLETENESS OF THE EVENT RECORD (EITHER COMPLETE OR PARTIAL). A PARTIAL EVENT IS ONE THAT IS PARTIALLY ERASED. THIS MAY OCCASIONALLY HAPPEN TO THE LAST EVENT IN THE INFUSER'S MEMORY BECAUSE THE OLDEST INFORMATION IS ERASED WHEN THE INFUSER'S MEMORY BECOMES FULL. | COMPLETE |

FIG. 7A

CCA: ICU
MEDICATION: DOPAMINE 400 mg / 250 mL

| TYPE OF ALERT PRESENTED | NUMBER | USER RESPONSE | | |
|---|---|---|---|---|
| | | OVERRIDE-YES | OVERRIDE-NO | CONFIRM PROGRAM -NO |
| LOWER HARD LIMIT | 7 | 4 | 2 | 1 |
| LOWER SOFT LIMIT | 14 | 5 | 6 | 3 |
| UPPER SOFT LIMIT | 3 | 3 | 0 | 0 |
| UPPER HARD LIMIT | 3 | 0 | 2 | 1 |
| TOTAL | 27 | 12 | 10 | 5 |

FIG. 7B

MEDICATION: HEPARIN 25,000 UNITS / 250 mL

| TYPE OF ALERT PRESENTED | NUMBER | USER RESPONSE | | |
|---|---|---|---|---|
| | | OVERRIDE-YES | OVERRIDE-NO | CONFIRM PROGRAM -NO |
| LOWER HARD LIMIT | 10 | 4 | 5 | 1 |
| LOWER SOFT LIMIT | 13 | 5 | 6 | 2 |
| UPPER SOFT LIMIT | 1 | 1 | 0 | 0 |
| UPPER HARD LIMIT | 4 | 0 | 1 | 3 |
| TOTAL | 28 | 10 | 12 | 6 |

FIG. 7C

MEDICATION: INSULIN (REGULAR) 100 UNITS / 100 mL

| TYPE OF ALERT PRESENTED | NUMBER | USER RESPONSE | | |
|---|---|---|---|---|
| | | OVERRIDE-YES | OVERRIDE-NO | CONFIRM PROGRAM -NO |
| LOWER HARD LIMIT | 8 | 5 | 2 | 1 |
| LOWER SOFT LIMIT | 14 | 5 | 2 | 7 |
| UPPER SOFT LIMIT | 5 | 3 | 0 | 2 |
| UPPER HARD LIMIT | 2 | 1 | 1 | 0 |
| TOTAL | 29 | 14 | 5 | 10 |

FIG. 7D

MEDICATION: VANCOMYCIN 500 mg / 100 mL

| TYPE OF ALERT PRESENTED | NUMBER | USER RESPONSE | | |
|---|---|---|---|---|
| | | OVERRIDE-YES | OVERRIDE-NO | CONFIRM PROGRAM -NO |
| LOWER HARD LIMIT | 7 | 4 | 2 | 1 |
| LOWER SOFT LIMIT | 11 | 5 | 6 | 0 |
| UPPER SOFT LIMIT | 9 | 1 | 8 | 0 |
| UPPER HARD LIMIT | 9 | 1 | 8 | 0 |
| TOTAL | 36 | 11 | 24 | 1 |

MEDICATION: DOPAMINE 400mg / 250mL

| TYPE OF ALERT PRESENTED | CCA | NUMBER | USER RESPONSE | | |
|---|---|---|---|---|---|
| | | | OVERRIDE- YES | OVERRIDE- NO | CONFIRM PROGRAM - NO |
| LOWER HARD LIMIT | ICU | 8 | 1 | 0 | 7 |
| LOWER HARD LIMIT | MEDSURG | 4 | 0 | 0 | 4 |
| LOWER SOFT LIMIT | ICU | 11 | 0 | 11 | 0 |
| LOWER SOFT LIMIT | MEDSURG | 5 | 5 | 0 | 0 |
| UPPER SOFT LIMIT | ICU | 2 | 0 | 0 | 2 |
| UPPER SOFT LIMIT | MEDSURG | 5 | 3 | 5 | 0 |
| UPPER HARD LIMIT | ICU | 3 | 0 | 0 | 0 |
| UPPER HARD LIMIT | MEDSURG | 5 | 0 | 4 | 1 |
| TOTAL | | 43 | 9 | 20 | 14 |

FIG. 8B

MEDICATION: HEPARIN 25,000 units / 250mL

| TYPE OF ALERT PRESENTED | CCA | NUMBER | USER RESPONSE | | |
|---|---|---|---|---|---|
| | | | OVERRIDE- YES | OVERRIDE- NO | CONFIRM PROGRAM - NO |
| LOWER HARD LIMIT | ICU | 12 | 5 | 0 | 7 |
| LOWER HARD LIMIT | MEDSURG | 6 | 2 | 0 | 4 |
| LOWER SOFT LIMIT | ICU | 11 | 0 | 11 | 0 |
| LOWER SOFT LIMIT | MEDSURG | 10 | 0 | 2 | 8 |
| UPPER SOFT LIMIT | ICU | 14 | 14 | 0 | 0 |
| UPPER SOFT LIMIT | MEDSURG | 4 | 2 | 0 | 2 |
| UPPER HARD LIMIT | ICU | 4 | 0 | 4 | 0 |
| UPPER HARD LIMIT | MEDSURG | 3 | 0 | 3 | 0 |
| TOTAL | | 64 | 23 | 20 | 21 |

FIG. 8C

MEDICATION: INSULIN (REGULAR) 100 units/100mL

| TYPE OF ALERT PRESENTED | CCA | NUMBER | USER RESPONSE | | |
|---|---|---|---|---|---|
| | | | OVERRIDE- YES | OVERRIDE- NO | CONFIRM PROGRAM - NO |
| LOWER HARD LIMIT | ICU | 8 | 1 | 0 | 7 |
| LOWER HARD LIMIT | MEDSURG | 4 | 0 | 0 | 4 |
| LOWER SOFT LIMIT | ICU | 11 | 0 | 11 | 0 |
| LOWER SOFT LIMIT | MEDSURG | 3 | 3 | 0 | 0 |
| UPPER SOFT LIMIT | ICU | 2 | 0 | 0 | 2 |
| UPPER SOFT LIMIT | MEDSURG | 1 | 1 | 0 | 0 |
| UPPER HARD LIMIT | ICU | 1 | 0 | 0 | 0 |
| UPPER HARD LIMIT | MEDSURG | 2 | 0 | 0 | 2 |
| TOTAL | | 32 | 5 | 12 | 15 |

FIG. 8D

MEDICATION: VANCOMYCIN 500 mg/100mL

| TYPE OF ALERT PRESENTED | CCA | NUMBER | USER RESPONSE | | |
|---|---|---|---|---|---|
| | | | OVERRIDE- YES | OVERRIDE- NO | CONFIRM PROGRAM - NO |
| LOWER HARD LIMIT | ICU | 10 | 2 | 1 | 7 |
| LOWER HARD LIMIT | MEDSURG | 7 | 0 | 3 | 4 |
| LOWER SOFT LIMIT | ICU | 11 | 0 | 11 | 0 |
| LOWER SOFT LIMIT | MEDSURG | 13 | 9 | 0 | 4 |
| UPPER SOFT LIMIT | ICU | 9 | 3 | 6 | 0 |
| UPPER SOFT LIMIT | MEDSURG | 6 | 0 | 3 | 3 |
| UPPER HARD LIMIT | ICU | 3 | 3 | 0 | 0 |
| UPPER HARD LIMIT | MEDSURG | | | | |
| TOTAL | | 59 | 17 | 24 | 18 |

Source List: Edit Rule Set

Drug Name: Acyclovir    Drug Class: None

Rule Sets: Full

Acyclovir 350 mg /50 mL Dosed in mL /hr

Drug Amount: 350    Drug Unit: mg    Diluent Amount: 50    Diluent Unit: mL

Dosing Unit: mL /hr    LHL: mL /hr: None    LSL: mL /hr: None    USL: mL /hr: 10    UHL: mL /hr: None Save    Cancel    Help

FIG. 15

| DRUG UNIT | DRUG AMOUNT RANGE | DILUENT UNIT | DILUENT AMOUNT RANGE | DELIVERY DOSE / RATE UNITS | DELIVERY DOSE / RATE HARD & SOFT LIMITS RANGE |
|---|---|---|---|---|---|
| RULE SETS = FULL | | | | | |
| mg, mcg, grams | 0.0–99.9; 100.–9999. NONE | mL | 0.0–99.9, 100.–9999. NONE | mcg / kg / min, mcg / kg / hr, mcg / min, mcg / hr, mg / kg / hr, mg / min, mg / hr, grams / hr, ng / kg / min | 0.000–0.999, 1.00–9.99, 10.0–99.9, 100.–999. NONE |
| | | | | mL / hr | 0.0–9.9, 10.0–99.9, 100.–999. NONE |
| mEq | 0.0–99.9; 100.–9999. NONE | mL | 0.0–99.9, 100.–9999. NONE | mEq / hr | 0.000–0.999, 1.00–9.99, 10.0–99.9, 100.–999. NONE |
| | | | | mL / hr | 0.0–9.9, 10.0–99.9, 100.–999. NONE |
| UNITS | 0.0–99.9, 100.–99999999. NONE | mL | 0.0–99.9, 100–9999, NONE | units / kg / hr, units / min, units / hr, mUn / min | 0.000–0.999, 1.00–9.99, 10.0–99.9, 100.–99999999. NONE |
| | | | | mL / hr | 0.0–9.9, 10.0–99.9, 100.–999. NONE |
| RULE SETS = LIMITED | | | | | |
| mg (NOT SET BY USER) | N / A | mL | 0.0–99.9, 100.–9999. NONE | mL / hr | 0.0–9.9, 10.0–99.9, 100.–999. NONE |
| RULE SETS = NONE | | | | | |
| mg, mcg, grams | N / A | N / A | N / A | mcg / kg / min, mcg / kg / hr, mcg / min, mcg / hr, mg / kg / hr, mg / min, mg / hr, grams / hr, ng / kg / min, mL / hr | N / A |
| MEq | N / A | N / A | N / A | mEq / hr, mL / hr | N / A |
| UNITS | N / A | N / A | N / A | units / kg / hr, units / min, units / hr, mUn / min, mL / hr | N / A |

FIG. 15A

| Commands | | | Queries and Responses | |
|---|---|---|---|---|
| StartLibraryUpdate | VLP | | QueryRevisionLevels | ARL |
| SetDrugLibrary | USL | | QueryRevisionLevelsResponse | BRR |
| EndLibraryUpdate | xEU | | ImpliedSchema | CMS |
| CalculateCCRC | cCC | | ExchangeSchema | yES |
| CommitDrugLibrary | gML | | QueryCCRC | MQC |
| Reboot | SRB | | QueryCCRCResponse | NQR |
| ClearDrugLibrary | eCD | | QueryDrugLibrary | OQL |
| | | | QueryDrugLibraryResponse | PQS |
| | | | QueryErrorCode | QQE |
| | | | QueryErrorCodeResponse | RQN |
| DrugLibrary | tDL | | ActiveLibrary | aAL |
| DrugEntryCount | hEC | | InstitutionName | EIN |
| | | | LibraryVersion | GLV |
| | | | ClinicalCareAreaCount | wAC |
| ClinicalCareArea | fCA | | InfuserSettings | DIS |
| AreaName | bAN | | KVORateMode | FKR |
| MaximumRate | JXR | | PiggybackMode | LPB |
| MaximumPatientWeight | IXW | | DelayStart | iDS |
| MinimumPatientWeight | KNW | | Callback | dCB |
| DefaultOcclusionPressure | HXP | | | |
| RuleSetCount | zRC | | | |
| RuleSet | TRT | | DrugEntry | rDE |
| DrugID | sDI | | DrugID | sDI |
| DosingUnits | pSU | | DrugName | uDN |
| DoseUpperSoftLimit | oUS | | DrugAmount | qDA |
| DoseLowerSoftLimit | mLS | | DrugUnit | vDU |
| DoseUpperHardLimit | nUH | | DiluentAmount | jLA |
| DoseLowerHardLimit | ILH | | DiluentUnit | WIL |
| DoseUnitsChangeAllowed | kUC | | | |

FIG. 20A

Source List: Add Rule Set

Drug Name: [DOBUTamine]    Drug class: [None ▷]

Rule Sets: [Full ▷]

DOBUTamine 500 mg / 250mL Dosed in mcg / kg / min

Drug Amount: [500]    Diluent Amount: [250]

Drug Unit: [mg ▷]    Diluent Unit: [mL ▷]

Dosing Unit: [mcg / kg / min ▷]

LHL: mcg / kg / min [0.5]    LSL: mcg / kg / min [0.75]    USL: mcg / kg / min [15]    UHL: mcg / kg / min [20]

[Add]    [Cancel]    [Help]

FIG. 21

SYSTEM FOR MAINTAINING DRUG INFORMATION AND COMMUNICATING WITH MEDICATION DELIVERY DEVICES

CROSS REFERENCE TO RELATED APPLICATIONS

This application claims priority based upon U.S. Nonprovisional application Ser. No. 10/783,877 filed Feb. 20, 2004 and U.S. Provisional Application Ser. No. 60/519,646 filed Nov. 13, 2003 and U.S. Provisional Application Ser. No. 60/527,550 filed Dec. 5, 2003, which are expressly incorporated herein in their entirety.

FIELD OF THE INVENTION

This invention relates in general to medication administration or delivery devices. More particularly, the present invention relates to a novel system for maintaining drug or medication information, providing communication between a computer and one or more infusion pumps, and assuring the integrity of such information and communication.

BACKGROUND OF THE INVENTION

Intravenous infusion therapy is prescribed where it is desirable to administer medications and other fluids directly into the circulatory system of a patient. Without alerts that warn the clinician that a higher or lower dose than clinical practice intended is being programmed, the resulting amount delivered to the patient can lead to increased morbidity or be fatal. There are various types of infusion pumps used by medical personnel to infuse medicinal fluids into a patient's body. There are very few pumps that have the feature of drug dose programming alerts. Some pumps use a customized drug library for electronically downloadable drug pumps. For example U.S. Pat. No. 6,269,340, which is incorporated by reference herein in its entirety, describes a system and computer readable medium for developing and downloading a customized drug library from a personal computer (PC) into an erasable, electronically loadable memory within the housing of a syringe pump. However, prior art systems and infusion pumps have several drawbacks. Following is a description of a novel infusion pump system that solves various problems found in the prior art.

SUMMARY OF THE INVENTION

The present invention relates to a system for communicating with one or more medication administration or delivery devices. More particularly, the invention relates to a system that utilizes a remote computer and a software program on a computer readable medium to download information to and/or upload information from one or more infusion pumps on a stand alone basis or as part of an integrated medication management system.

In one example, the software provides the remote computer with powerful drug library creation, editing, and archiving capabilities that can be used by a user, including but not limited to, a biomedical engineer, a pharmacist, a doctor, etc. A single drug formulary worksheet or database with each drug entry having an associated CCA designation can be created for the entire medical facility. The same drug may have different limits established in different clinical care areas and different device parameters and settings may be applied depending on the recommended best practices of the medical facility for a particular clinical care area. The single drug formulary worksheet is easier to control, update and maintain than a separate database or subdatabase for each clinical care area. In one example of the software, the software provides a real time rule set validator that dynamically validates entries into the drug formulary worksheet with each keystroke as the user keys in data. The user is instantly notified if a value exceeds an allowed range or if the data does not meet predetermined expected characteristics. In one example, the software also uses an extensible markup language for communications with the medication delivery devices. Communications between the computer and the devices may be validated using any desired technique(s), such as a cyclic redundancy check. In another example, a database is used to store the history of multiple infusion pumps. This enables the ability to retrieve the event log data from all pumps in one institution in one database, and being able to retrieve the data based on place of use, time, error types, etc. Other types of reports are also possible.

The software is useful, in one example, as a part of a system utilizing a computer to download information into and upload information from one or more medication delivery devices (such as infusion pumps). In one embodiment, the system includes a remote personal computer (PC) that has a memory for storing the software, a user interface, and display. The system also includes one or more infusion pumps and one or more techniques for connecting the PC to the pumps to facilitate the communication of information between the PC and the pumps. The infusion pumps can have single or multiple channels for delivering medications (i.e., fluids, medication, or mixtures thereof) to a patient. In one example, the information downloaded to the pumps can include, without limitation: a drug library with one or more drug entries typically grouped by clinical care area, drug delivery parameters (such as hard and soft limits), device settings, parameters or limits; patient specific information such as patient identification data; and caregiver specific information such as caregiver identification.

In one example, the software and the communication protocol utilize an open architecture that is adaptable to different versions, models and makes of medication delivery devices. In one embodiment of the present invention, the software is utilized in a system that establishes wired communication with a plurality of general purpose infusion pumps for downloading and uploading information. In other embodiments, the software is utilized in a system that establishes wireless communication with one or more general purpose infusion pumps having plug and play communication modules installed within the pump housing for downloading and uploading information. In other embodiments the plug and play communication module is integrally incorporated on an optional circuit board enclosed within the pump housing. Examples of medication delivery devices included, but are not limited to, single or multiple channel general purpose infusion pumps, patient controlled analgesia (PCA) pumps, ambulatory pumps, enteral pumps, IV infusion pumps, etc.

The software is also useful on a computer that interfaces with or acts as a medication management unit or server. In this example, the software facilitates communication between the PC and one or more medication delivery devices within a patient area network (PAN). Examples of what the communication between the PC and devices can be used for include, but are not limited to, downloading patient specific drug delivery instructions for operating and controlling the medication delivery device, and uploading information such as device characteristics, conditions, usage and alarm histories.

BRIEF DESCRIPTION OF THE DRAWINGS

The present invention is illustrated by way of example and not limitation in the figures of the accompanying drawings, in which like references indicate similar elements.

FIG. 6 is an example of a worksheet the pharmacist sees on the computer with the present invention.

FIG. 7 shows an example of a soft limit override report.

FIG. 7A is a table explaining the report of FIG. 7.

FIGS. 7B-7E and 8A-D show examples of a soft and hard limit override reports for several different drugs.

FIG. 15 is a diagram showing an example of a dialog box used when editing a rule set for a drug.

FIG. 15A is a table showing the valid entry ranges for various fields or values in the Rule Set Editor of the present invention.

FIG. 20A is a table showing the XML object tag names utilized in one example of the present invention.

FIG. 21 is an example of a dialog box used with the rule set editor when adding, editing, deleting, or viewing a rule set.

DETAILED DESCRIPTION

In general, the present invention provides a system and method for providing communication between a computer and one or more medication administering devices. The invention uses hardware and software to provide the link between the computer and the infusion pumps. In one example, the invention is designed for use in a pharmacy or biomedical technical service environment or in a Medication Management Unit (MMU) as described in applicant's co-pending provisional application Ser. No. 60/527,583 entitled MEDICATION MANAGEMENT SYSTEM, filed Dec. 5, 2003 and the regular patent application by the same title, filed Feb. 20, 2004, which are expressly incorporated herein in their entirety.

The invention allows a facility to customize a drug library for use with an infusion pump, such as a PLUM A+® infuser or pump, available from Abbott Laboratories in Abbott Park, Ill. Other types of pumps may also be used with the present invention. For example, the invention may be used with patient-controlled analgesia (PCA) pumps, ambulatory pumps, enteral pumps, as well as IV infusion pumps. The invention also provides for storage of data from multiple pumps and generates various safety reports, events and alarm reports.

Figure 1:
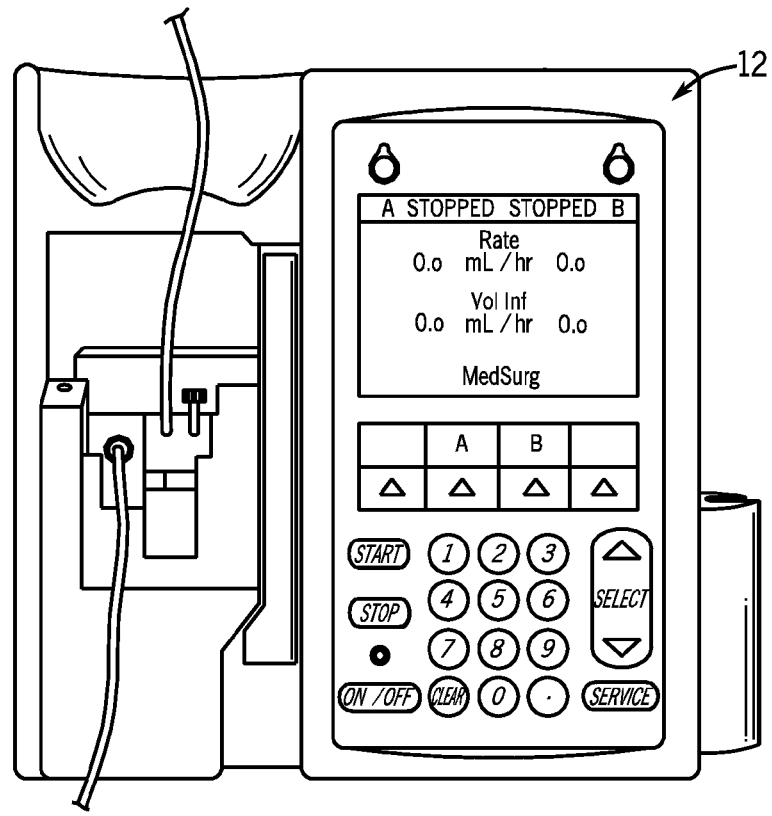
FIG. 1 is a front view of an infusion pump according to the present invention.
Figure 1A:
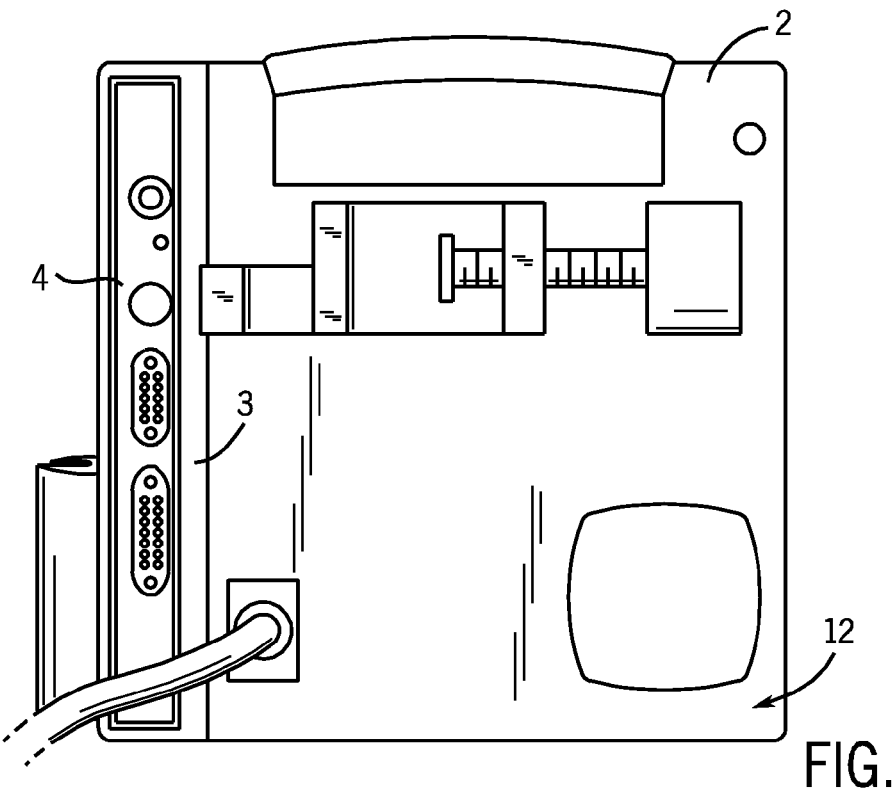
FIG. 1A is a rear view of the infusion pump of FIG. 1.
Figure 1B:
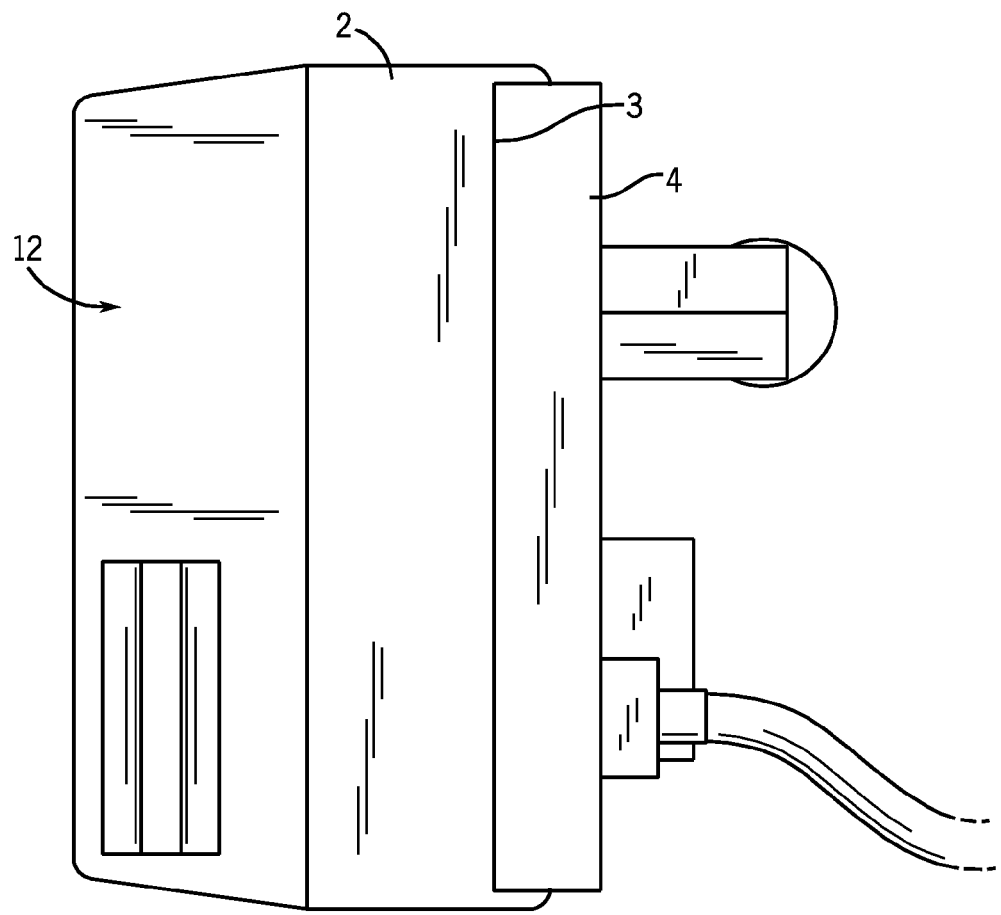
FIG. 1B is a rear perspective view of the infusion pump of FIG. 1 and shows the plug and play module that facilitates communication between the pump and the computer.
Figure 1C:
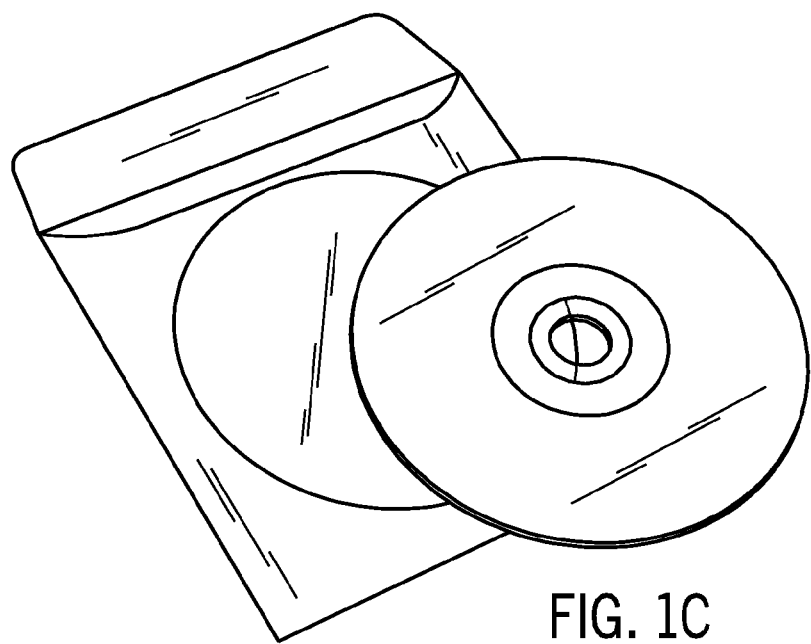
FIG. 1C is a front perspective view of a CD-ROM disk or one possible embodiment of a computer readable medium according to the present invention.
Figure 1D:
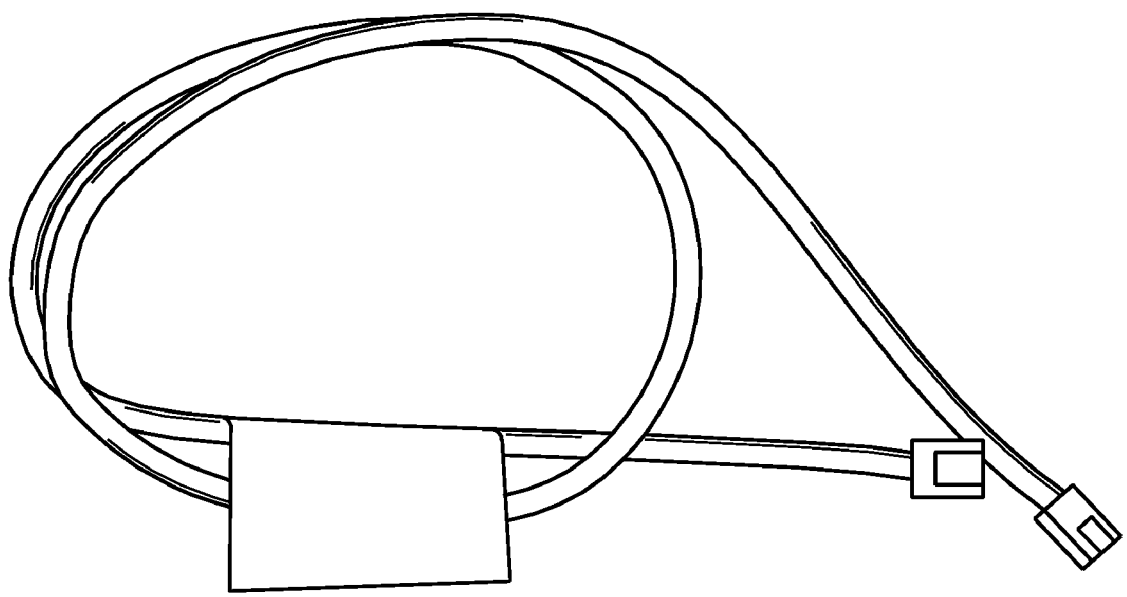
FIG. 1D is a perspective view of a data cable which can be used to bring multiple pumps into communication with the computer through connection to a junction box.

FIG. 1 is a front view of an Abbott PLUM A+® infuser or pump 12. FIG. 1A is a rear view of the PLUM A+® pump of FIG. 1 wherein the housing 2 has been modified to include a vertically elongated slot 3 formed therein for receiving a plug and play module 4 inside the housing 2 to facilitate the communication between the computer and the infusion pumps. The plug and play module 4 is operatively disposed inside the housing 2 and substantially enclosed, protected and insulated by the housing. The plug and play module 4 has a thin, elongated card-shaped case that fit into the slot 3 of the pump housing 2. Thus, the plug and play module 4 of the present invention does not substantially increase the space occupied by the pump. The plug and play module 4 shown in FIGS. 1A and 1B is adapted for hard-wired communication. However, as discussed below, the plug and play module 4 can also be adapted for wireless communication.

In one example, software of the present invention can store up to twelve Clinical Care Areas (CCAs) with up to 100 drug entries (99 drug entries and No Drug Selected) in each CCA for a total of 1200 entries in the Master Drug Formulary. In this example, the software of the present invention supports data transfer of up to fifteen Abbott PLUM A+® Single-Channel Infusers connected to a single computer. Of course, the invention can be designed with different storage and communication capabilities and be adapted for different pumps.

Figure 2:
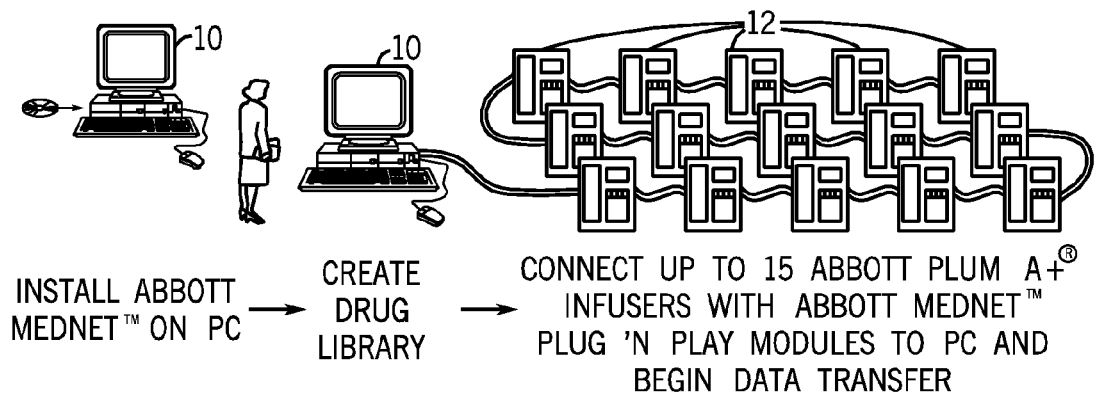
FIG. 2 is a diagram illustrating how the present invention may be used.

FIG. 2 is a diagram illustrating how the present invention may be used. As shown in FIG. 2, once the software is installed on a host computer (in this example, a personal computer or PC 10), a user can create a drug library (or use a library provided with the software media), including any desired rule sets. The drug library may include entries including drug name, drug amount, drug unit, diluent amount, diluent units, dosing units, drug class, hard limits and soft limits within the hard limits. It is not necessary to enter the drug concentration because this value is derivable from the drug amount, drug unit, diluent amount and diluent units. A user may also create a plurality of CCAs within the library. Next, the user can connect the PC to a plurality of infusers 12 and begin data transfer between the PC and the infusers. For example, the active drug library can be downloaded from the PC to the connected infusers. In addition, data can also be transferred from the infuser to the PC. For example, event and alarm logs can be uploaded from connected infusers to the PC. Any other desired type of data or communications can also be transferred between the PC and infusers.

Figure 3:
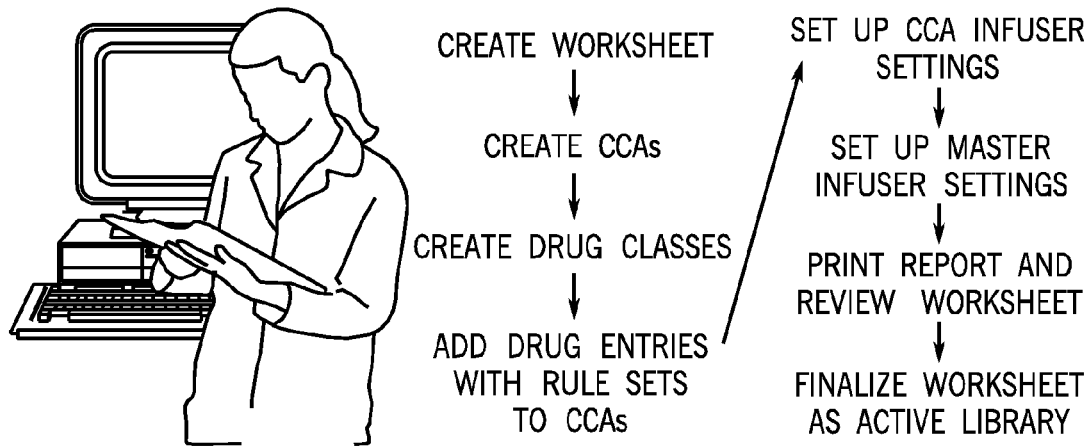
FIG. 3 is a diagram illustrating one example of a process for customizing a library.
Figure 6:
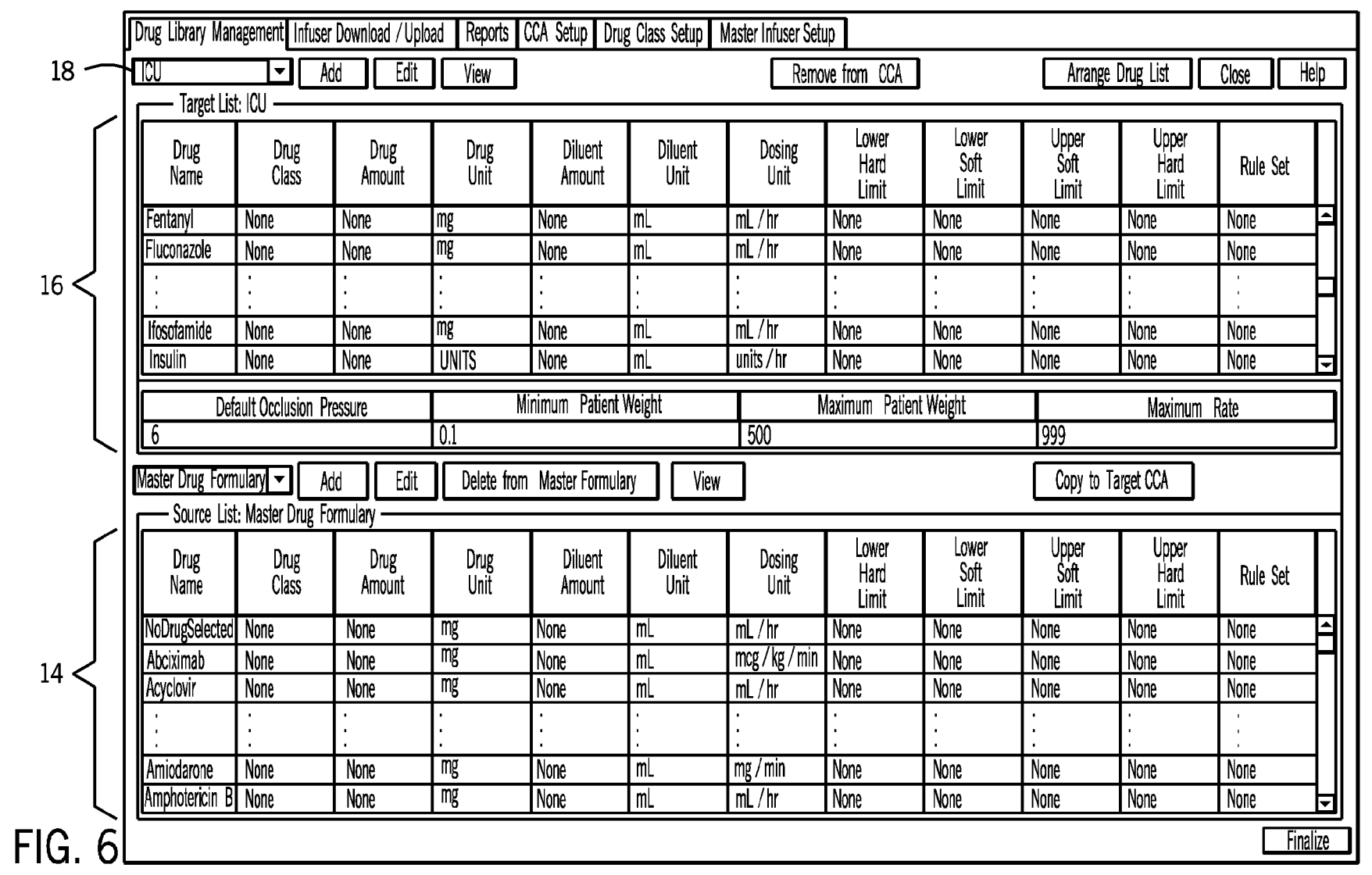

FIG. 3 is a diagram illustrating one example of a process for customizing a library. The process of FIG. 3 begins with a user, such as a pharmacist, creating a worksheet on a PC 10. In this example, a worksheet can be thought of as a library that can still be edited and has not yet been finalized. One salient feature of the worksheet is that it provides two simultaneous views: a target "working" formulary view and a source "reference" formulary view. In one example, a master formulary view of the drugs can be in the reference view, while at the same time, a view of target drugs for the CCA is shown. Likewise, in another example, the target view could be one CCA such as "Medical" while the source is another CCA such as "Surgery". The pharmacist is able to copy the exact same drug entry with its associated rule sets from the source to the target. This presentation reduces the time it takes to develop all the necessary CCAs and promotes easy quality checks for the pharmacist and a view across all the drug rule sets being developed. In addition there is a reduction in typing errors if one was forced to reenter the same drug name, concentration and rule sets in numerous different CCAs. Errors in developing a drug library can lead to a reduced safety net for the nurses and increased patient morbidity. FIG. 6 shows one example of a worksheet that a pharmacist (or other user) may see on a computer with the present invention. FIG. 6 shows a split screen view, with a master drug formulary table on the bottom portion 14 of the screen, and the drugs in the selected CCA on the top portion 16 of the screen. A pull down menu 18 is used to select which CCA is viewed in the top portion 16.

Figure 20:
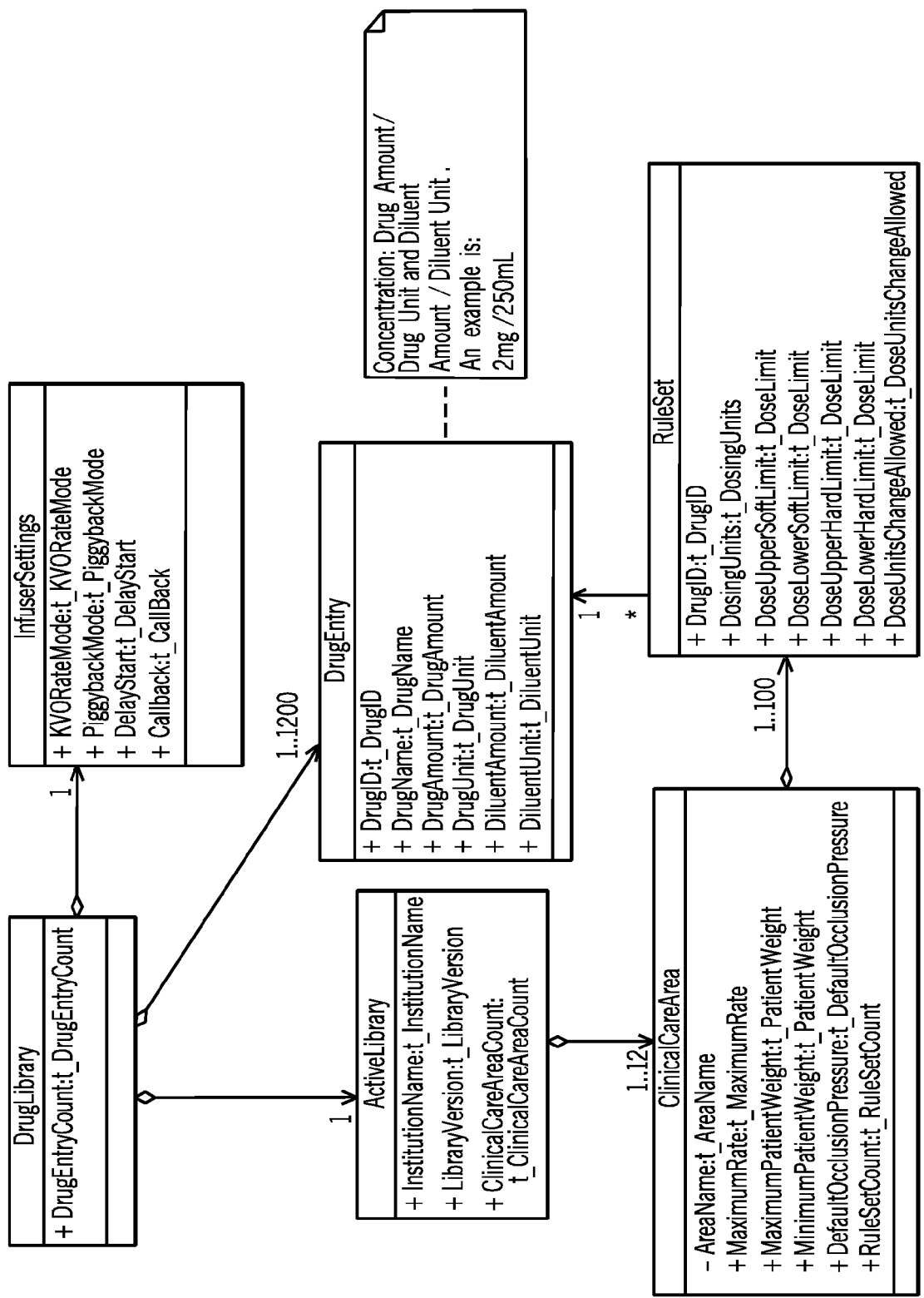
FIG. 20 is a diagram of one example of the XML exchange schema.

Referring to FIGS. 3 and 20, the user next creates a CCA (if one is not already created), which is a subset of a drug library for use in an area or patient population of the hospital (e.g., Intensive Care Unit (ICU)), as defined by an authorized user. Each CCA can have a predefined number of specific drugs. Also, a hospital can have a plurality of CCAs in a drug library. Next, the user creates any desired drug classes (for example, antibiotics, narcotics, beta blockers, etc.) and then adds drug entries with rule sets to CCAs. Next, the CCA infuser settings are set. Examples of CCA infuser settings include maximum rate, default occlusion pressure, and maximum and/or minimum patient weight. Next, master infuser settings are set up. Examples of master infusion settings include Continue Rate (the default rate the infuser switches to after a therapy has completed), Enable Delay/Standby (the default stand by setting), Callback Notification (when enabled, causes the infuser 12 to emit an audible nurse callback alarm and display a notification between steps during a multi-step infusion or after loading a dose), and Deliver Together (allows you to choose as a default the 2-channel delivery method). Before finalizing the worksheet, a worksheet report can be printed and reviewed. Finally, the worksheet is finalized as the active library.

Figure 1E:
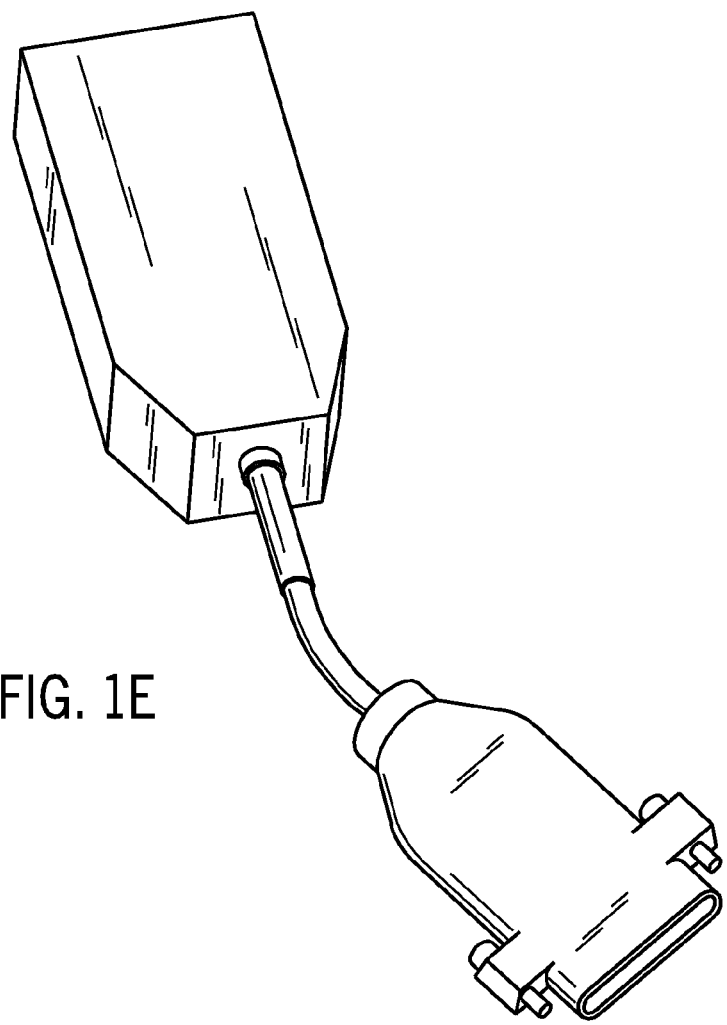
FIG. 1E is a perspective view of a dual jacked junction box cable for connecting the pump plug and play module to the computer and interconnecting to other pumps.
Figure 1F:
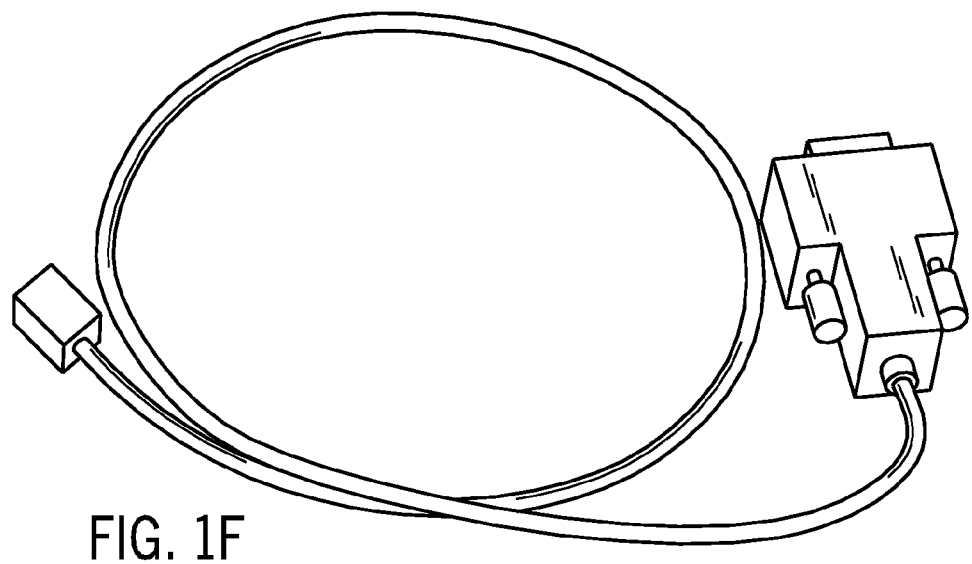
FIG. 1F is a perspective view of a data cable for connecting the computer to one of the dual jacks on the junction box.
Figure 4:
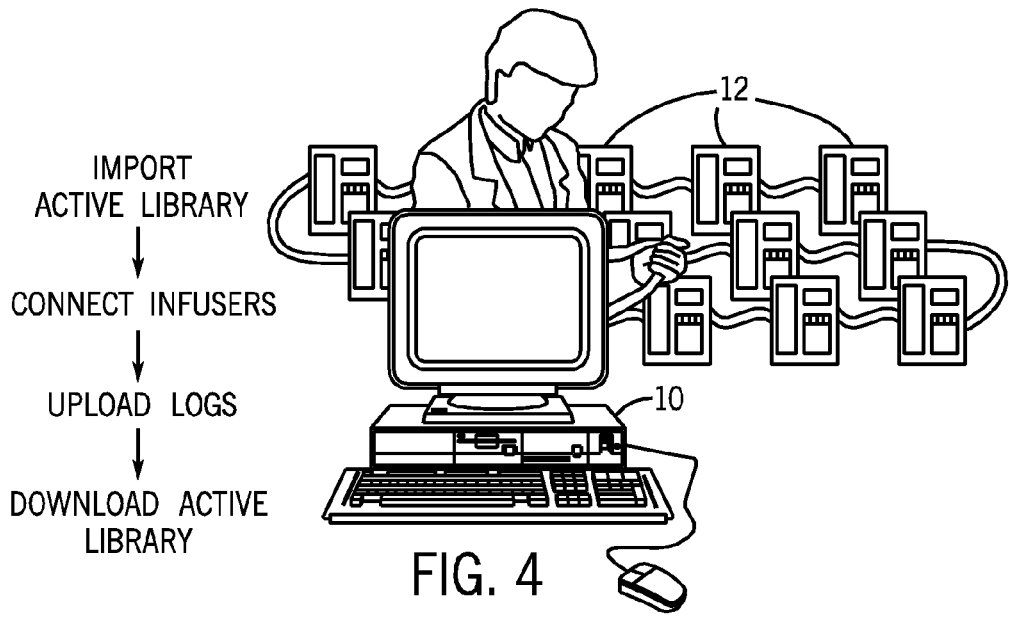
FIG. 4 is a diagram illustrating the communication between the PC and infusion pumps.
Figure 5:
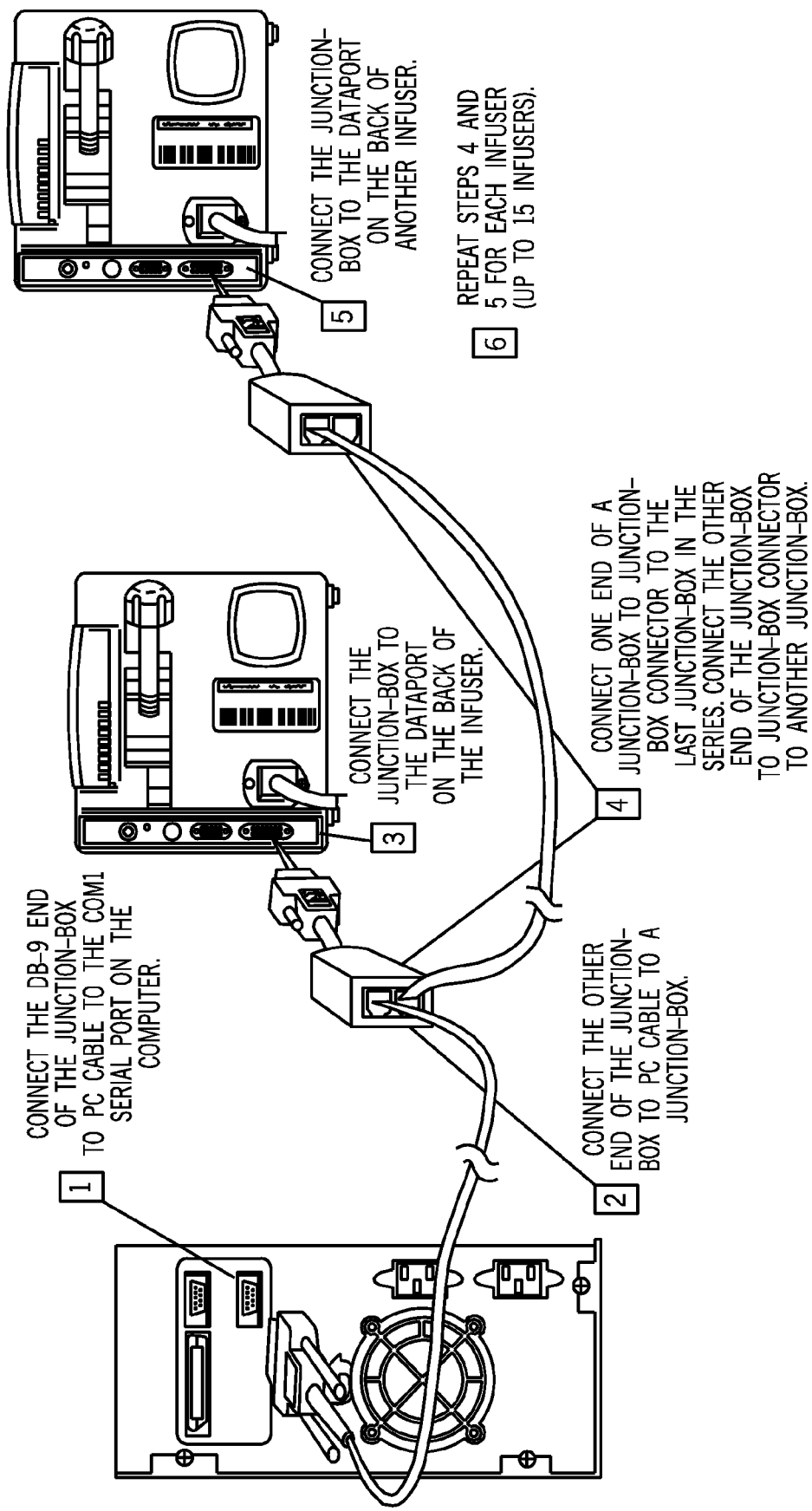
FIG. 5 is a rear view depicting the connection of a plurality of pumps to the computer.

After an active library is ready, a technician can connect one or more infusers 12 to the PC 10 for data transfer. FIGS. 4 and 5 are diagrams illustrating the communication between the PC 10 and the infusers 12. First, the active library is imported. Next, the technician connects the infusers 12 to the PC 10. The infusers 12 can be connected to the PC 10 in any desired manner. For example, a cable (FIG. 1F) can be connected between a serial port on the PC 10 and a junction box (FIG. 1E), which is also connected to the data port of each infuser 12 through the plug and play module 4 (FIG. 1A). The infusers 12 and PCs 10 can use any desired type of interfaces including serial interfaces (RS232, USB, etc.), parallel interfaces, etc. In another example, the infusers 12 can have wireless capabilities to provide a connection to the PC 10 as needed. Once connected, information including but not limited to programming events, settings, and alarms, etc. can be uploaded to the PC as historical information (logs) or real-time information, and the active library can be downloaded to all of the infusers 12. FIG. 5 is a diagram illustrating the connection of a plurality of pumps to a computer using a serial cable with a plurality of serial connectors and a plurality of junction boxes.

Figure 4A:
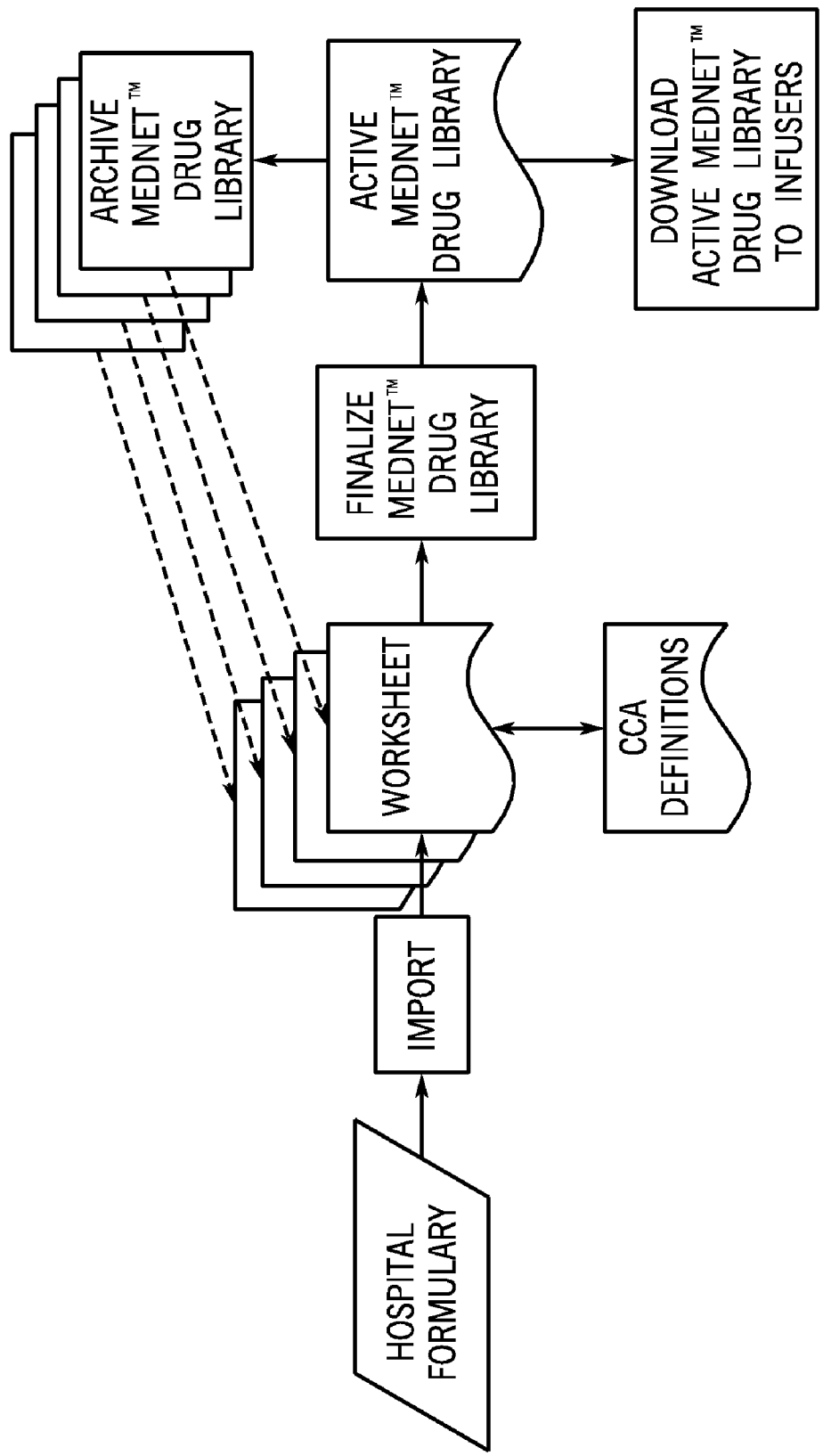
FIG. 4A is a flow diagram illustrating the process of editing and downloading a drug library.

FIG. 4A is another flow diagram illustrating the process described above. As shown, a hospital formulary can be imported into one or more worksheets. After a user finalizes a drug library, the active drug library can be downloaded to one or more infusers. FIG. 4A also illustrates that drug libraries can be archived and used again when developing or editing worksheets.

The present invention includes several features that solve various problems in the prior art. Following is a description of these features.

The present invention makes use of Extensible Markup Language (XML) representation for Remote Procedure Calls (RPC). One benefit of using XML is that the use of XML syntax documents allows the protocol to support different types of products. For example, a first infuser may only allow a certain communication format that is different from that required by another infuser. By using XML, the system can communicate with different types of infusers. Examples of different types of devices include devices with different computer architectures, devices running different types of computer processors, devices running different software programs (or different versions of the same program). In addition, some devices operate using a binary data format that may be incompatible with the binary format used on other devices. In this way, the host computer can use the same message formats for various different types of devices. The invention also provides the use of an XML parser in communicating with a patient-connected medical device, such as an infusion pump.

In some applications of the present invention, the host and the pump may have incompatible binary data formats. For this reason, it is necessary to define a lexical form that is the same on the host and the pump. This common lexical representation is called the canonical form. The process of converting from the processor-specific binary form to the canonical form is called canonicalization.

Error checking commonly uses checksum or hash functions. However, these functions are not always reliable. Since the present invention uses medically critical data, it is important to use a more reliable error checking function. In addition, it is desirable to allow partial library updates (such as an individual item in the drug library), while still being able to validate the content of the entire library. The present invention supplements standard checksum or hash function with a Global Canonical Cyclic Redundancy Check (gCCRC) which guards the state of the entire exchange data structure. Its purpose is to allow the host and pump to verify that their data is the same after attempted data transmission. The gCCRC can detect errors that are not trapped by lower level checksum and other methods. For example, the gCCRC can detect when the number of packets dropped is exactly the range of sequence numbers. The gCCRC also provides a final "backstop" validation against every sort of protocol failure, including exceptions like pump disconnection, power failure, and software defects.

In one example, rather than the conventional approach of comparing two binary images (an image at the host computer and an image at the infuser) to see if they are the same to validate the content of data stored in the infuser, a comparison is made to determine whether two possibly entirely different physical (bit-wise) representations are semantically the same.

This is accomplished by using a canonical representation (which neither side actually uses for storage) and then doing the comparison between the two abstract representations. For example, to validate the contents of data in the infusion pump, a CRC is calculated based on the data in the pump. Next, a CRC is calculated based on what the host thinks the data in the pump is. Next, these numbers are compared. If the numbers are the same, it is highly likely that the data is the same at the host and at the infuser. One advantage to this approach is that only a small amount of data is required to be transferred for comparison purposes. A binary image of the entire library does not need to be retransmitted for comparison. This approach also eliminates the requirement of error checking during data transmission.

Another aspect of the present invention relates to how the CRC is calculated. The form of CRC used is specified by the Comite Consultatif Internationale de Telegraphique et Telephonique (CCIT). However, with the present invention, the CCIT CRC is done in the opposite bit order (right to left, versus left to right as specified by CCIT) so as to make the computation more efficient. It turns out that since Intel processors have the opposite "endianness" from the so-called "network byte order" prescribed by the CCIT, the bit reversal avoids some implementation problems on some processors.

When constructing the words (which may have different endianness) described above using CRC, it is important to precisely define the syntax of the document or data before using CRC. The present invention uses XML schema for this purpose. In addition, XML schema is used to define the semantics used for validation). The data to be validated (e.g., a drug library) is converted to its canonical form (described above) and validated and verified using the XML schema to determine whether the data is both valid and well formed. In the example of a library, this validation check occurs before transmitting the library to the pump.

One example of the XML schema of the present invention includes two main parts, exchange schema and implied schema. Generally, the exchange schema defines the structure of data to be communicated between a host computer and an infusion pump. The implied schema defines (and validates) the types of data being exchanged.

FIG. 20 is a diagram showing one example of the XML exchange schema, using unified modeling language (UML) notation. As shown in the example of FIG. 20, a drug library includes infuser settings, at least one drug entry, and active library objects. In this example, there is only one infuser settings object and one active library object, but up to 1200 drug entry objects. Each object shown in FIG. 20 contains attributes as described in its respective box. The active library object includes up to 12 CCA objects. Each CCA object includes up to 100 rule set objects. In this example, there is only one rule set per drug, although multiple drugs can share a single rule set. The data structures shown in FIG. 20, and their members, are defined as an XML object with tag names (which are optionally abbreviated/compacted) for each entry. FIG. 20A identifies the names used in one example. FIG. 20A shows commands along with queries and responses, and their corresponding abbreviations. As shown, in addition to the data structures, the commands and queries are also encoded in XML, and are processed the same as data by the host computer (or server) and pump (or client) sides. As is apparent to one skilled in the art, the commands and queries can be used with the present invention to efficiently provide communication between a host computer and a client infusion pump. For example, the following command ends drug library updates, while communicating the server's calculated global canonical checksum to the client (<xEU gccrc="9B8D"/>). As shown in FIG. 20A, "xEU" is the abbreviation for the command "EndLibraryUpdate", while the value "9B8D" is an example of a hexadecimal value of the server's checksum. The other commands and queries are used in a similar manner.

The implied data is a contract between the host computer 10 and the infusion pump 12. The implied data is managed by the host and used when developing software for the host and clients. In one example, the implied data is not transmitted over the communications link, nor does the infuser software ever process it. One purpose of the implied schema is to validate the value and types of data that are allowed to be passed to the client. One form of validation is range checking to restrict out of range values from being transmitted. Another form of validation can be display accuracy. For example, the display range of a variable can be tenths of digit. In such cases, sending a value of 12.00 would be invalid as it describes accuracy beyond the range of the variable. Another type of validation may be specific type checking. The implied schema takes the form of an XML schema document. The XML schema document provides type definitions for all the client/host specific type definitions in the exchange schema. The following are examples of various implied schema types. The first example is a simple string type schema, which defines an institution name string to be 30 characters or less.

```
<?xml version="1.0" encoding="UTF-8"?>
<xs:schema xmlns:xs="http://www.w3.org/2001/XMLSchema">
    <!-- defines t_InstitutionName as a 30-character string -->
    <xs:simpleType name="t_InstitutionName">
        <xs:restriction base="xs:string">
            <xs:maxLength value="30"/>
        </xs:restriction>
    </xs:simpleType>
</xs:schema>
```

XML schema supports fixed-point representations directly through a fractionDigits facet on most numeric data types. The following examples define minimum and maximum decimal and fraction digit values.

```
A fixed point type specification
<xs:simpleType name = "t_DefaultVTBI">
    <xs:restriction base = "xs:decimal">
        <xs:minInclusive value = "0.1"/>
        <xs:maxInclusive value = "999.0" />
        <xs:fractionDigits value = "1" />
    </xs:restriction>
</xs:simpleType>
```

In one example, the present invention constructs an implied enumeration by defining an xs:enumeration restriction over an EncodedString.

```
A MESA implied enumeration t_DosingUnits
<xs:simpleType name="t_DosingUnits">
    <xs:restriction base="EncodedString">
        <xs:enumeration value="mL/hr" encoding="0"/>
        <xs:enumeration value="mcg/kg/min" encoding="1"/>
        <xs:enumeration value="mcg/kg/hr" encoding="2"/>
        <xs:enumeration value="mcg/min" encoding="3"/>
        <xs:enumeration value="mcg/hr" encoding="4"/>
        <xs:enumeration value="mg/kg/hr" encoding="5"/>
        <xs:enumeration value="mg/min" encoding="6"/>
        <xs:enumeration value="mg/hr" encoding="7"/>
```

```
        <xs:enumeration value="grams/hr" encoding="8"/>
        <xs:enumeration value="ng/kg/min" encoding="9"/>
        <xs:enumeration value="units/kg/hr" encoding="10"/>
        <xs:enumeration value="units/min" encoding="11"/>
        <xs:enumeration value="units/hr" encoding="12"/>
        <xs:enumeration value="mUn/min" encoding="13"/>
        <xs:enumeration value="mEq/hr" encoding="14"/>
    </xs:restriction>
```

Multiple ranges for a single value can be specified for a value via the <xs:choice> tag. The following examples relate to a patient weight field, including upper and a lower ranges.

```
t_PatientWeight
    <xs:group name="t_PatientWeight">
        <xs:choice>
            <xs:element name="PatientWeight"
                type="t_PatientWeight_0"/>
            <xs:element name="PatientWeight"
                type="t_PatientWeight_1"/>
        </xs:choice>
    </xs:group>
t_PatientWeight_0
    <xs:simpleType name = "t_PatientWeight_0">
        <xs:restriction base = "xs :decimal">
            <xs:minInclusive value = "100"/>
            <xs:maxInclusive value = "500"/>
            <xs:fractionDigits value = "0"/>
        </xs:restriction>
    </xs:simpleType>
t_PatientWeight_1
    <xs:simpleType name = "t_PatientWeight_1">
        <xs:restriction base = "xs:decimal">
            <xs:minInclusive value = "0.1"/>
            <xs:maxInclusive value = "99.9"/>
            <xs:fractionDigits value = "1"/>
        </xs:restriction>
```

One issue with using XML is that XML is very verbose, which increases bandwidth requirements. To reduce communications overhead, the invention uses a more compact form of XML that is still standard compliant, but operates with significantly reduced bandwidth by abbreviating the XML identifiers to a few character mnemonics. The encoding is well formed XML that uses terse element and attribute names. In one example, each XML Short Name may consist solely of alphabetic characters and be uniquely identified by its first character. The commands pass arguments as XML attributes. The responses return values as attribute values and/or as elements nested inside the response element. For example, the long XML name "InfuserSetting" is shortened to "IS". So, an exemplary line of commands might look like this:

Example: Compact PumpConfiguration Instance

```
<IS>
    <FKR>1</FKR>
    <LPB>0</LPB>
    <iDS>true</iDS>
    <dCB>true</dCB>
    <HXP>6</HXP>
</IS>
``` rather than the non-compact version, which would look like this:

Example: PumpConfiguration Instance

```
<InfuserSetting>
    <KVORateMode>KVO</KVORateMode>
    <PiggybackMode>CONCURRENT</PiggybackMode>
    <DelayStart>true</DelayStart>
    <Callback>true</Callback>
    <DefaultOcclusionPressure>6</DefaultOcclusionPressure>
</InfuserSettings>
```

In this example, the encoding reduced approximately 200 characters to approximately 60 characters, yielding a ratio of about 3.3 to 1.

The present invention uses an extended data port protocol that includes a reliable binary transport protocol on top of the data port protocol. In other words, a protocol is run over the data port protocol. One advantage of this approach is improved compatibility between different machines. Another advantage is that large messages can be segmented and reassembled. This allows very large messages to be sent through the protocol stack, even if the host or pump cannot handle large messages. A large message will be segmented into small packets and later reassembled.

The invention assures the safety of the database by allowing only one library to be maintained in the computer that can be downloaded to pumps and is termed the active library. This assures that the wrong library is not downloaded over time. A library that can be edited is termed a worksheet and many different worksheets can exist. A library that was once active and is no longer active is archived and automatically designated as such. To be able transfer an active library to another computer a unique special file extension and recognition was developed. This allows for the transfer of the exact same library between pharmacies of a larger health care facility that may have multiple sites.

Another advantage of the present invention is that the system is capable of simultaneously downloading data to a plurality of infusion pumps. The library is transmitted in a multicast fashion to multiple pumps. The system will periodically verify the status of each pump using point to point communication. If one of the pumps has a problem, the download can be restarted, and each pump will be notified of the new download. In one example, when a pump detects a download error during a broadcast download, the pump sends a message to the host computer, which then halts the download. The host then polls all of the pumps to determine the point where all of the pumps received messages with valid data. Since the download takes place over multiple individual tagged messages, a tag number allows the host computer to identify the point where no pumps had reported a download error. When the download is continued, the download begins at this point, so all of the data does not have be downloaded again. The multicast communication strategy optimizes the download throughput. For example, if a library takes 10 minutes to download, 15 pumps can received the download in 10 minutes, as opposed to the 150 minutes it would take to download to each pump individually. This blend of multicast and point-to-point communication facilitates a robust download and a retry/recovery mechanism to individual pumps. Another advantage of the current invention is that the worksheet provides the pharmacists with a master formulary view at the same time providing for a CCA view of drug entries. Editing and copying of drug entries can be done in either view. This presentation promotes easy quality checks, a safety feature, for the pharmacist as drug or dosing limit alerts being developed. Errors in developing a drug library can lead to a reduced safety net for the nurses and increased patient morbidity.

Another advantage of the present invention is that a single database can be used to store the history of multiple infusion pumps. This enables the ability to retrieve the event log data from all pumps in one institution in one database, and being able to retrieve the data based on place of use, time, error types, etc. Other types of reports are also possible. Also, even with a centralized database, the system can include multiple PCs, which can each download to any desired pumps.

Similarly, the present invention is capable of collecting pump use data and generating related reports. For example, soft limit override data can be collected for the generation of a report relating to soft limit overrides. This type of report can be used for any desired purpose such as evaluating personnel, setting future limits, etc.

The present invention includes an active drug library editor that can validate drug data in real time. The invention is capable of managing an unlimited number of drug libraries. Drug libraries are configured with a Master Drug Formulary (the drug table from which CCAs are created) and multiple CCAs. Libraries can be active (a worksheet that has been finalized), archived (a previously active library that has been saved to the database) or a worksheet (a draft library that has not yet been approved for download to infusers and can still be edited). Only active libraries are allowed to be downloaded to a pump. Items such as configuration parameters that describe the operational behavior of a pump can be set pump-wide or specific to a CCA. These parameters are unique to each library. TallMan lettering is supported for drug names. Changes to TallMan lettering is replicated throughout a library. Each drug in the library is associated with a drug classification. Drug classifications are unique to each library. A drug may have multiple concentrations and multiple rule sets. Rule sets can be full, limited, or none.

Another feature of the present invention relates to the various levels of rules that the active drug library can utilize. The present invention allows the use of multiple rule levels including device rules (e.g., rules relating to the operation or limitations of a particular medical device or type of device), CCA rules (e.g., rules relating to the particular CCA), drug rules (rules relating to the particular drugs), and patient rules (e.g., rules relating to particular patients such as age, weight, health, medical history, allergies, etc.).

The Rule Set Editor (RSE) is used to create and edit rules sets in a drug database. RSE is responsible for accurately displaying rule sets and enabling the "Add", "Save" or "Delete" buttons when appropriate. FIG. 21 shows an example of a dialog box used with the RSE when adding, editing, deleting, or viewing a rule set. As shown in FIG. 21, there are fields for drug name, drug class, drug amount, drug diluent, and soft/hard limits. RSE is responsible for adjusting its input criteria and validating a rule set while a user is making input selections. RSE uses RuleSetDataItem (RSDI) (described below) as a data model and RuleSetValidator (RSV) (described below) as a controller. RSE sends a message to RSDI when the model should be validated. RSDI, in turn, sends a message to RSV to validate RSDI. This separation of responsibility is established to encapsulate a standard validation implementation for both the rule set editor user interface and the library import process.

Another advantage of the present invention relates to the drug configuration. The present invention includes a special rule set that allows the definition of a drug name and concentration for a particular drug. However, at the pump, a user can override the drug amount and drug unit. So, a limit is set, but a user is allowed to define the concentration. Therefore, the invention has the ability to selectively limit or allow the user to select the units of delivery on a drug-by-drug basis, and the ability to label a drug with concentration in drug units, but deliver in other units (such as ml/hr).

Another advantage of the present invention relates to constraint definitions. The invention includes a set of unique constraint objects. A constraint object defines a standard implementation for validating keyboard, mouse and import inputs. For example, a particular field may be constrained to a numerical range. The constraints prevent things from being done incorrectly. However, sometimes one object input is based on the content of another object and with the present invention constraint definitions change dynamically as input definitions change. For example, for the object "drug amount", the constraint can change depending on the units of measure (e.g., grams, etc.).

Dose Rate Document (DRD) aggregates multiple constraints so that input verification can be cascaded through an unlimited number of constraint objects. In one example of an implementation of a DRD, the object DoseRateDocument extends javax.swing.text.PlainDocument to implement the required method insertString(int offset, String string, AttributeSet attributes). This method internally invokes StringConstraint.checkInput(String proposedValue) when appropriate.

Rule Set Constraints (RSC) provide specific DRDs for drug amount, diluent amount, and hard and soft limits RSC are used to change these settings dynamically to validate inputs based on drug unit and dosing unit. RSC aggregates several constraint objects to verify that entries are within valid ranges. In one example, drugAmount, diluentAmount, and limits have their own DRD and Constraint object, but each is unique to meet the targets needs. RSC is initialized with default values when constructed. Successive calls to setDrugAmountConstraints(drugLabelPK) adjust the drugAmount DRD. Similarly, calls to setDiluentAmountConstraint( ) adjust the diluentAmount DRD. In one example of the present invention, the only constraint is diluentAmount. Likewise, successive calls to setLimitConstraints(dosingUnitPK) adjust the limit amounts.

Rule Set Data Item (RSDI) is a specialized DataItem and acts as a data model. Getter/Setters are provided to get and set attributes in the various forms needed by RVDC (described below), RSE and RSV (described below). DataItems know how to add themselves into a SQL Server database. In one example of the present invention, RSV is implemented as a static object and not a private implementation of RSDI. This separation of responsibility makes the implementation and maintenance of RSV simpler.

Rule Set Data Model (RSDM) is a specialized AbstractDataModel that provides a virtual data store for all RSDI items that are being imported.

Rate Versus Dose Calculations (RVDC) calculate the delivery rate corresponding to a given dose, in the context of such variables as patient weight, drug concentrations, etc. In one example, RVDC is not tied to a particular infusion pump implementation. Also, in one example, the RVDC algorithm is purely algebraic. RSDI owns the data that is extracted by RSV and passed to RVDC to calculate either calculateDoseFromRate or calculateRateFromDose.

The Rule Set Validator (RSV) orchestrates the validation process for all rule set data fields. The RSV starts by resetting the constraints needed by drugAmount, diluentAmount and the limits. It systematically validates each field for conformance, as follows:

Length cannot be zero or blank and cannot exceed the maximum length.

Pixel length cannot exceed displayable area on pump.

Name is checked for invalid characters.

RSV is used to validate rule sets from different sources, including: user input, imported libraries, copied drugs from one location to another, and makes adjustments to CCA maximum rate settings. RSV is consistently and constantly used throughout the system to validate that a rule set is well formed, valid and will not violate the delivery conformance for the entire library. If a user attempts to enter data that violate a rule, the "save" button in the dialog box will be dimmed and disabled, forcing the user to change the data that violates the rule. FIG. 15 is a diagram showing an example of a dialog box used when editing a rule set for a drug. In this example, the user edits whatever is desired, and then clicks the "save" button. If the entries are not valid, the "save" button will be dimmed and the user will not be allowed to save the changes.

Figure 16:
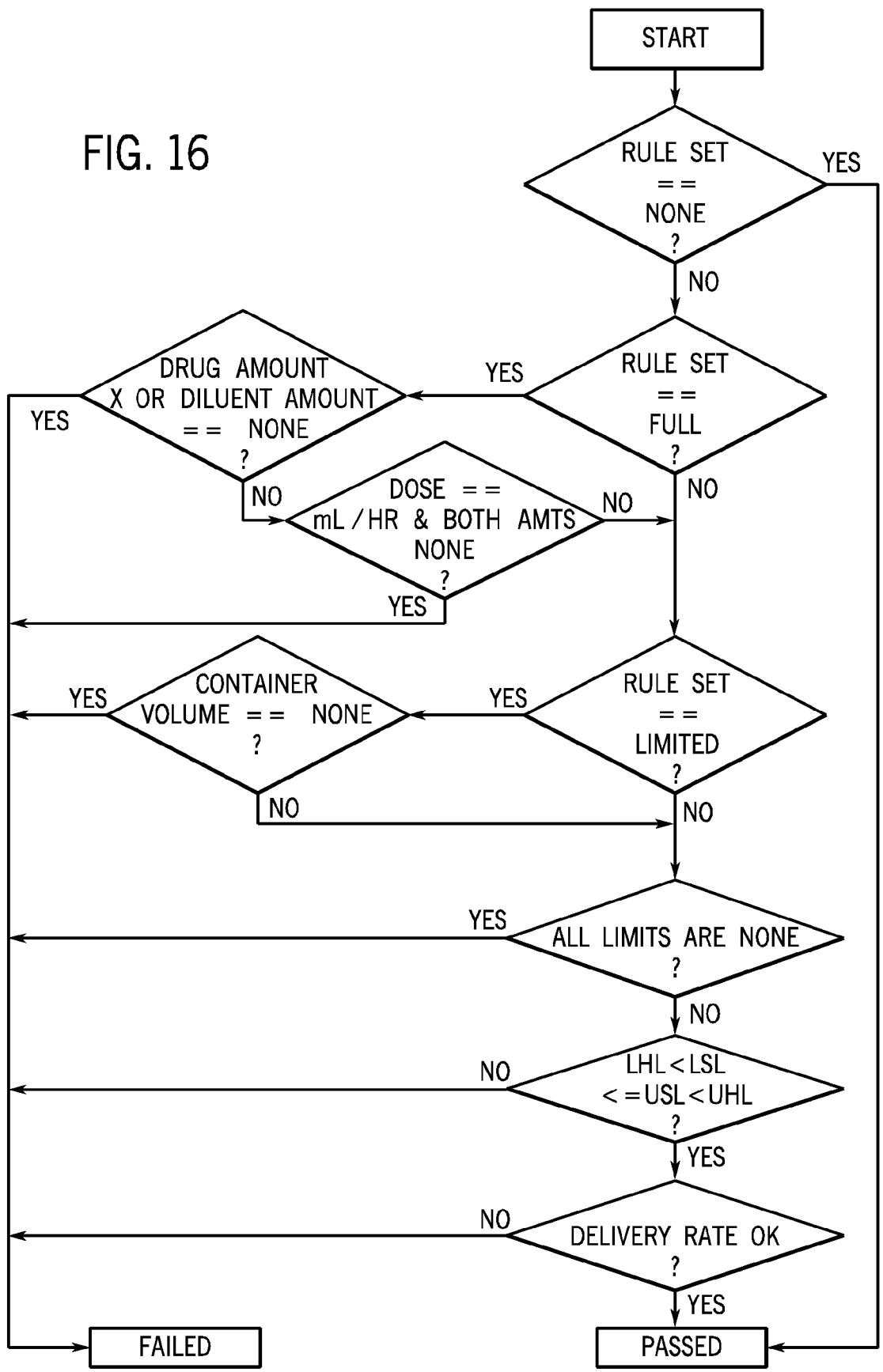
FIG. 16 shows one example of a rule set validator decision tree.

FIG. 16 shows one example of a rule set validator decision tree. The decision tree shown in FIG. 16 describes the basic logic used to assess the validity of rule set limits Generally, the decision tree asks if the rule set is equal to "NONE", "FULL", or "LIMITED", and then asks the other questions outlined in the decision tree to determine if the rule set is valid. FIG. 16 illustrates the dynamic checking that is done each time a user makes a keyboard or mouse entry while making or editing a rule set. FIG. 16 also shows how the RSV checks to see if such a delivery rate/dose would be acceptable based upon the dose limits. Other settings may also factored in or analyzed in a similar manner, such as the maximum rate CCA infuser setting.

Figure 22:
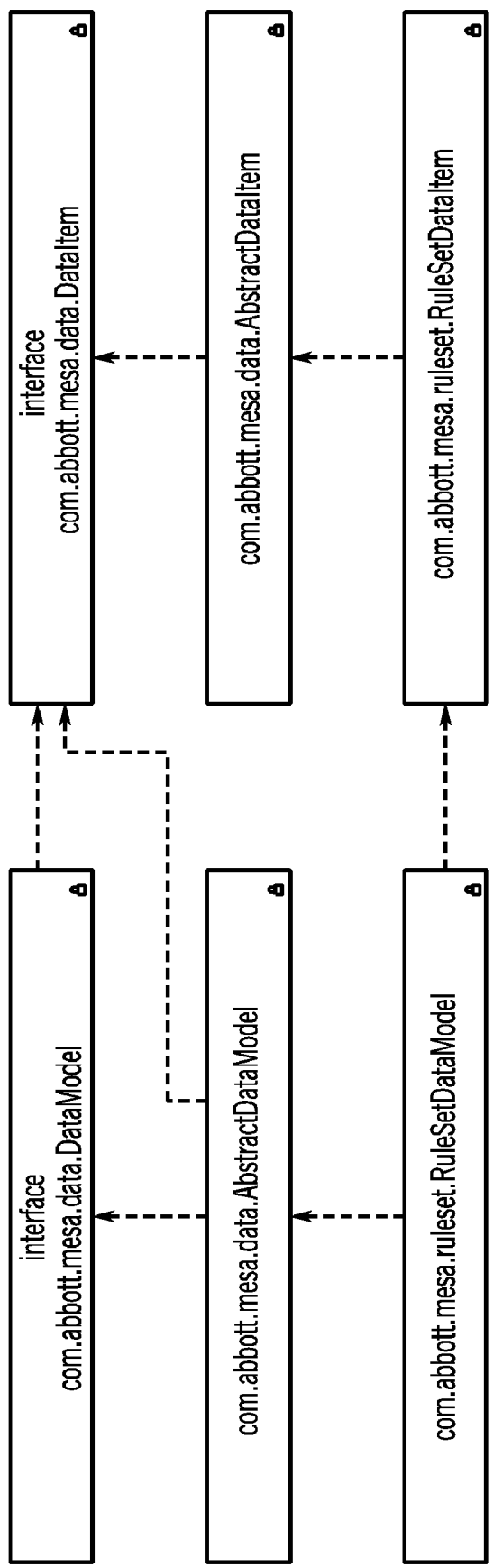
FIG. 22 is a block diagram illustrating the relationship between a DataModel and DataItem.
Figure 23:
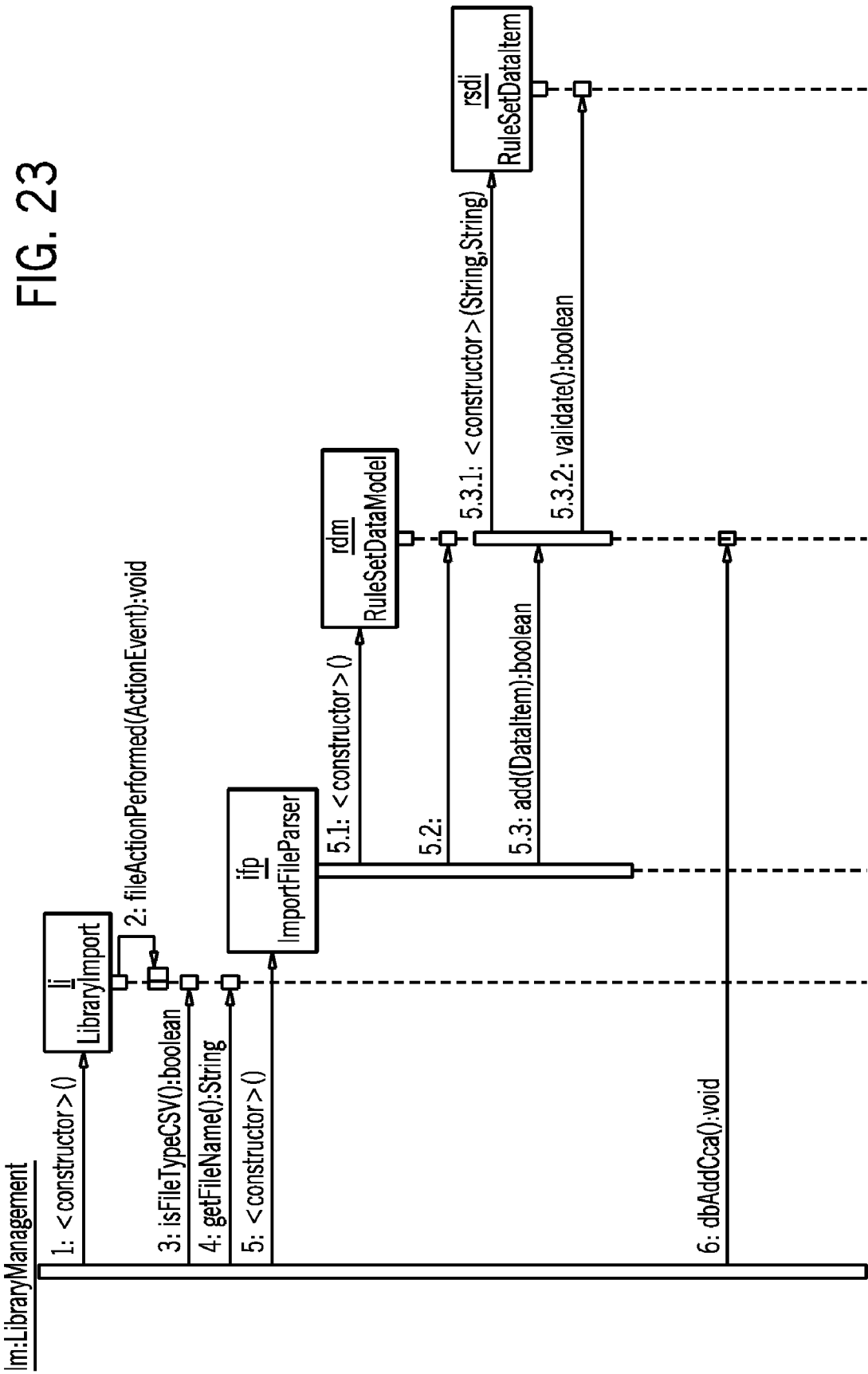
FIGS. 23-25 are diagrams illustrating the high-level interactions between various processes of the present invention.
Figure 24:
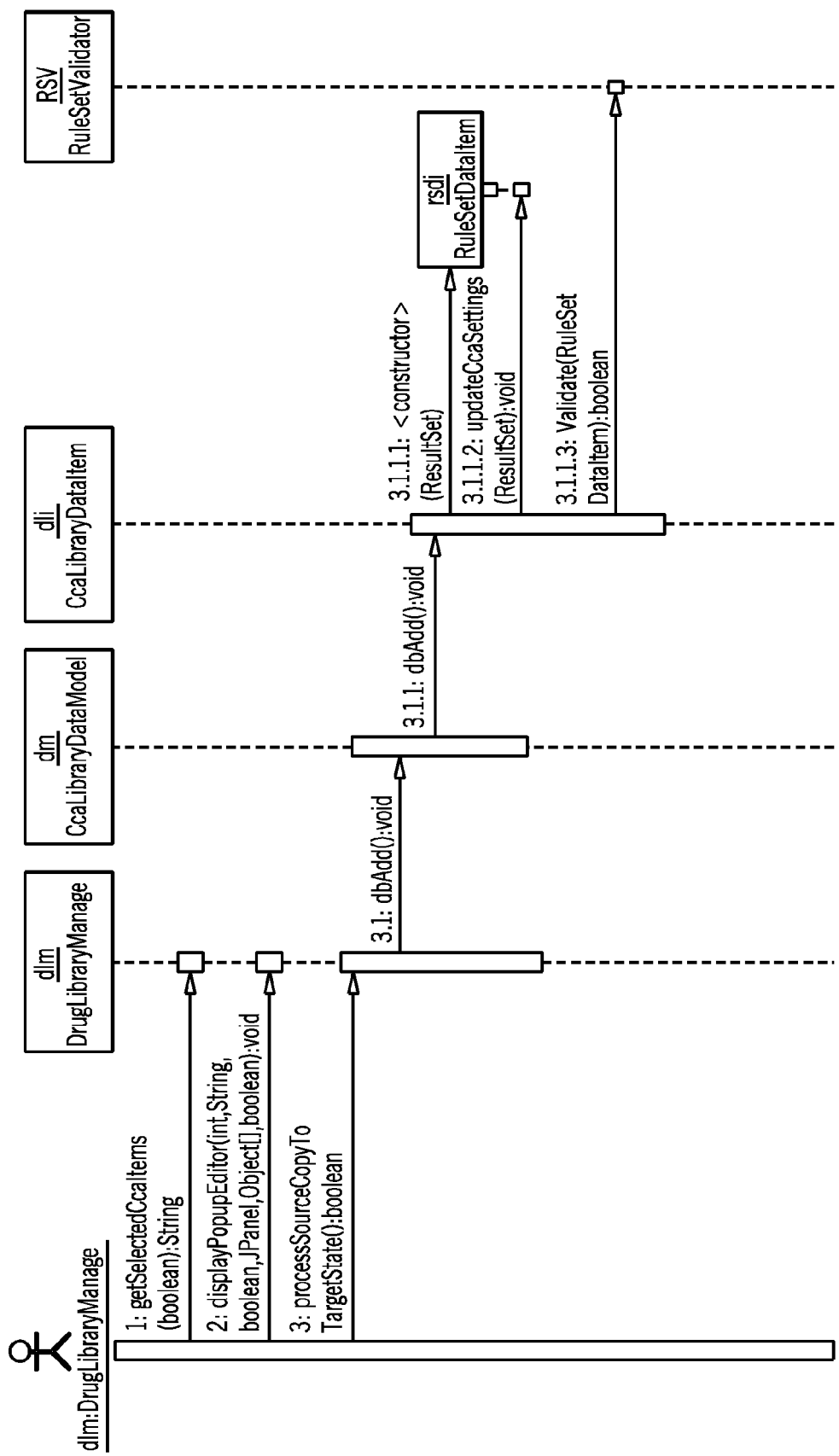
Figure 24A:
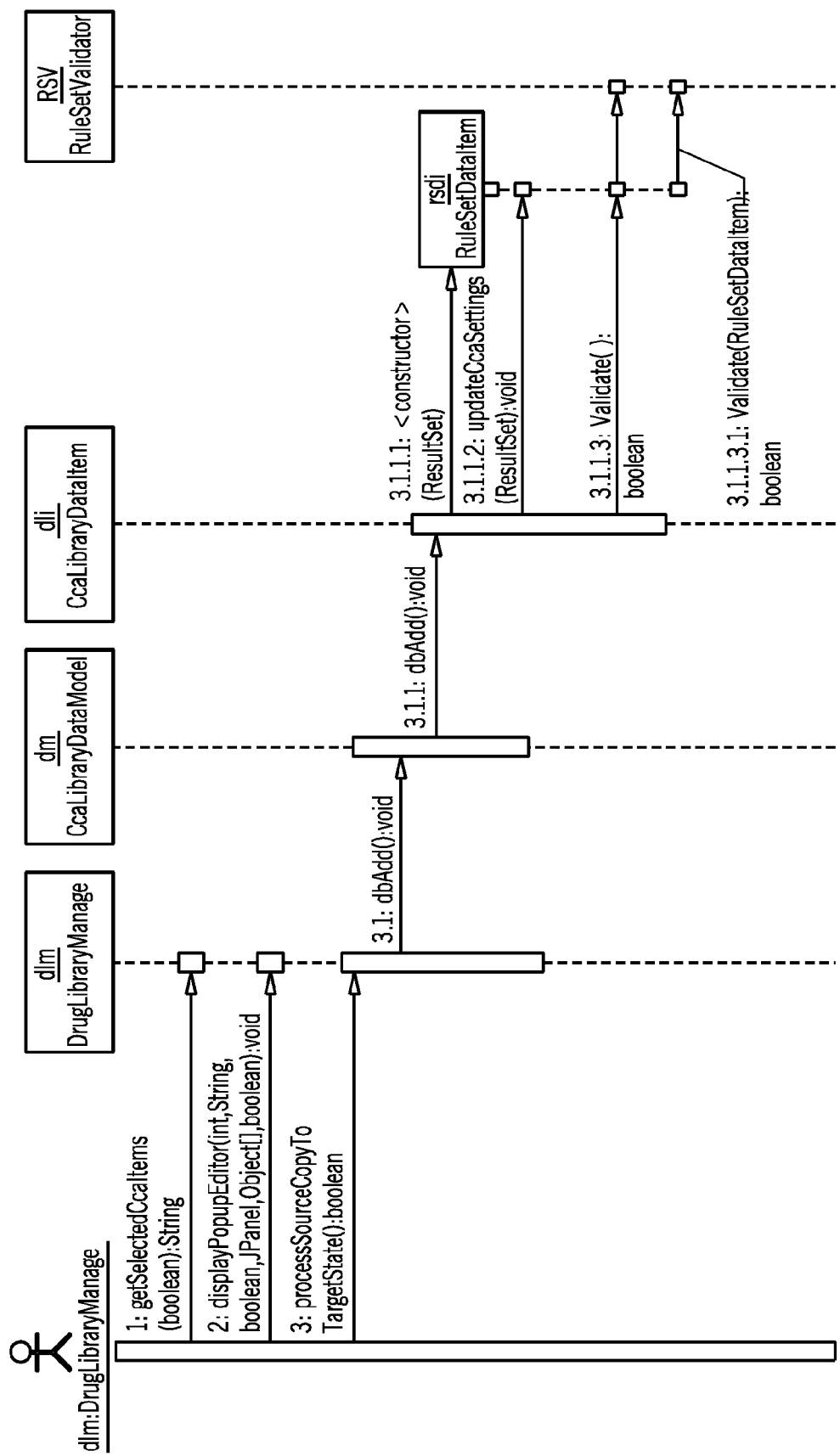
Figure 25:
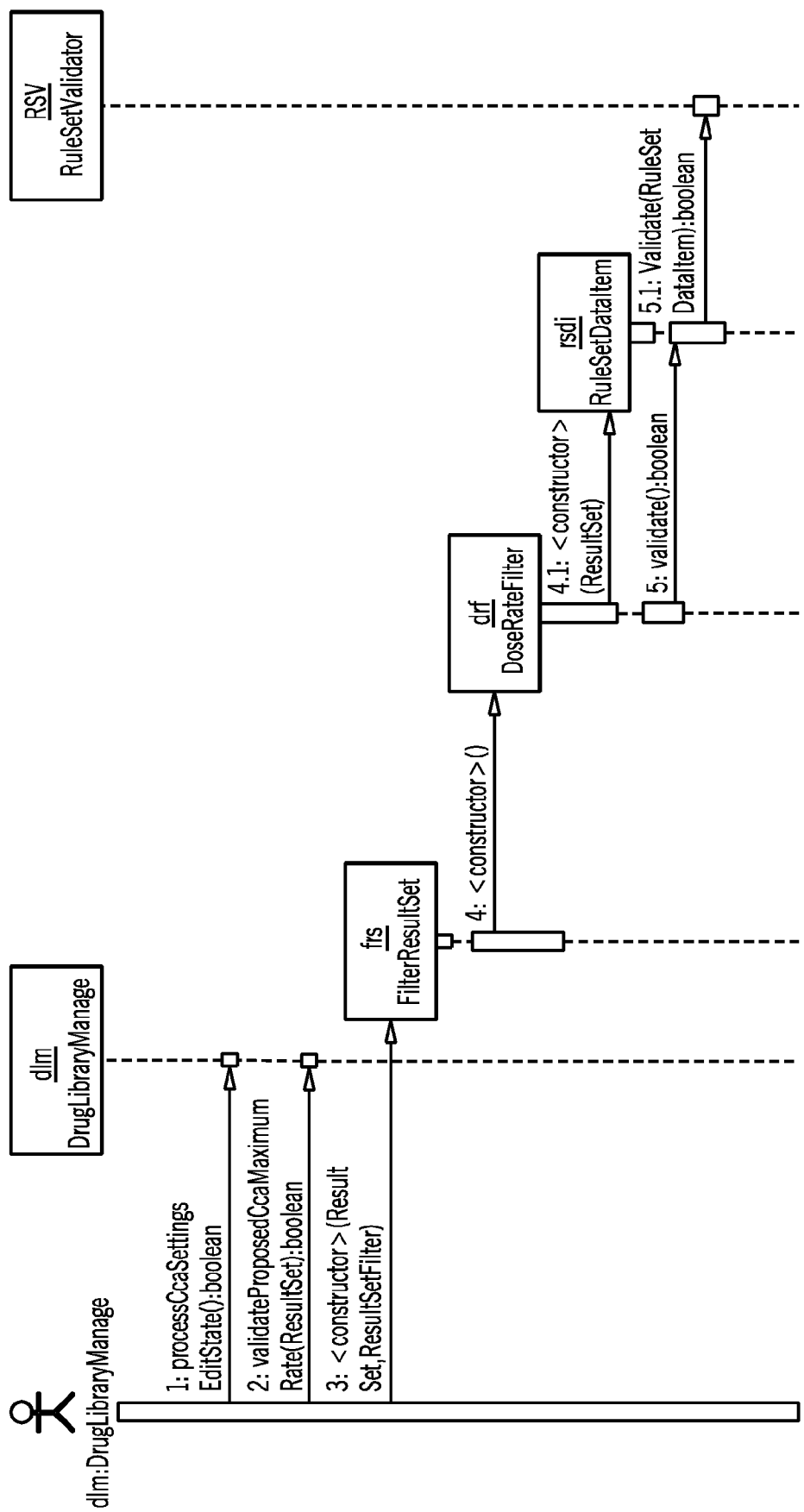

Another feature of the present invention relates to Data Models. Data Models are used to import data into a drug library, copy from a source to a destination CCA library, and to edit CCA settings within a CCA Library. The following figures illustrate the relationship and high-level interactions between DrugLibraryManager (DLM) and RSDI. FIG. 22 shows the relationship between a DataModel and DataItem. For clarity, CCASettings and CCALibrary DataModel and DataItem are not shown in FIG. 22. FIG. 23 is a diagram illustrating the high-level interaction between the import process and RuleSetDataItem. As mentioned above, there are some similarities between an import and the RSE. For example, RSDI is validated by RSV. The import process consumes either a tab separated value (TSV) or a comma separated value (CSV) file, creating an RSDM object. RSDM is used to create a Drug Library, CCA, CCA Library View, and Master Drug Formulary (MDF) entries. FIGS. 24 and 24A show two preferred UML diagrams illustrating the high-level interaction between DrugLibraryManager (DLM) and RSDI when rule sets are copied from a target to a source CCA Library. Similarly, FIG. 25 illustrates the high-level interaction between DrugLibraryManager (DLM) and RSDI when CCA Settings are edited in the target CCA Library.

The present invention also has a specialized combo box editor called the Dose Rate Editor (DRE). The DRE is used to establish the DRD for drugAmount, diluentAmount and the limits The DRE is unique because it makes special allowances for both dose rate input and the reserved word 'None'. The DRE converts all absolute values of zero (e.g., "0", "0.0", "0.00", "none", etc.) to 'None' and strips off any trailing zero or decimal points for non-zero values.

As mentioned before, the present invention is capable of using both hard and soft limits simultaneously. In addition, various related reports can be generated from one or more infusion pumps. One type of report is a soft limit override report (discussed below). Following is an example of how soft limit override reports can be generated. Persistent storage design for SoftLimit Alert/Override report is driven by both specific requirements for the "saving" of the uploaded logs and by the indirect requirements for parsing the raw log data to identify clinical action, partial events, and duplicate log entries. In one example, all log data maintains an association with the Infusion pump from which it was uploaded.

Raw log data is persisted both for archiving purposes and to support direct reporting (listing) of the log contents. Prior to its persistence, the raw log data undergoes a first pass of parsing to remove those portions of the log that represent old data that has already been uploaded to the PC but remained stored in the infusion pump (because the log is not cleared following an upload). The following database tables are defined to hold the parsed log data.

| Table Name | Purpose |
| --- | --- |
| UploadHistory | A record in this table represents a specific session involving the upload of event log data from an Infuser. |
| UploadEvent | A record in this table represents a single, raw event as captured by, and uploaded from, the Infuser. |
| EventType | A look up table of log event type of interest to the PC application |
| ClinicalAction | A record in this table represents a single attempt to execute a program to administer a drug. Note that a clinical event is only recorded in the database if it results in the occurrence of a reportable event. |

The first three tables listed, UploadHistory, UploadEvent, and EventType, support the existing functionality to persist the raw uploaded event data. The fourth table listed, ClinicalAction, is intended to provide the necessary context for an individual event (the Soft Limit Alert/Override) to generate a meaningful and useful report.

The individual fields of each of the tables described above are illustrated as follows. First, the fields from the UploadHistory are listed, along with a description of their purpose.

| Field Name | Purpose |
| --- | --- |
| UploadHistoryID | A unique (sequential) identifier for an upload session. This is the Primary Key for the table. |
| SerialNumber | A unique identifier for the Infuser from which the upload was taken. This is a Foreign Key to the Pump table (existing). |
| CompositeVersion | This field holds the information necessary to uniquely identify the Library installed on the Infuser |
| DateUploaded | The Date (and time) when the upload was successfully completed. |
| State | Identifies the current state of the upload process. Possible states include Uploaded, Consumed (completely parsed and persisted) |

Next, the fields from the UploadEvent are listed, along with a description of their purpose.

| Field Name | Purpose |
| --- | --- |
| UploadEventID | A unique (sequential) identifier for an uploaded event. This is the Primary Key for the table. |
| UploadHistoryID | The identifier of the UploadHistory from which this event was created. Foreign Key to the UploadHistory table. |
| EventTypeID | The type of the event. Foreign key to the EventType table. |
| EventDate | The date stamp for a single log as uploaded from an infuser |
| EventData | The contents forsingle line of raw data as uploaded from an Infuser. |
| DateCreated | The time that the event is added to the database. |

Next, the fields from the EventType are listed, along with a description of their purpose.

| Field Name | Purpose |
| --- | --- |
| EventTypeID | A unique (sequential) identifier for an event type. This is the Primary Key for the table. |
| EventName | The name of the event. Note this table holds event types that are of interest to the PC application for the purposes of parsing reportable events. This will be a subset of the event types produced by the Infuser. |
| DateCreated | The date that the item is added to the database. |

Finally, the fields from the ClinicalAction are listed, along with a description of their purpose.

| Field Name | Purpose |
| --- | --- |
| ClinicalActionID | A unique (sequential) identifier for a clinical action. This is the Primary Key for the table. |
| UploadHistoryID | The identifier of the UploadHistory from which this clinical event was parsed. This is a Foreign Key to the UploadHistory table. |
| UploadEventID | A unique (sequential) identifier for an uploaded event. |
| CcaName | The name of the clinical care area programmed for this action. |
| Status | Indicating whether all the data for this action was available in the log (Complete). Partial if only partial data was available. |
| Attempted Dose | The dose value that user input. |
| ProgrammedDose | The dose that is being delivered. |
| SoftLimit | The dose limit value |
| DosingUnits | The current dose units |
| SoftLimitType | Indicates the softlimt is upper or lower limit |
| OverrideType | Indicates the softlimitOverride type is alert or override |
| InfuserChannel | The current infuser channel |
| StepNumber | The step that the softlimit is violate |
| DrugName | The drug name programmed for this action. |
| DrugConcentration | The drug concentration programmed for this action. |
| DeliveryConfirmedProgramConfirmed | Indicates whether or not the delivery program was confirmed. |

Figure 26:
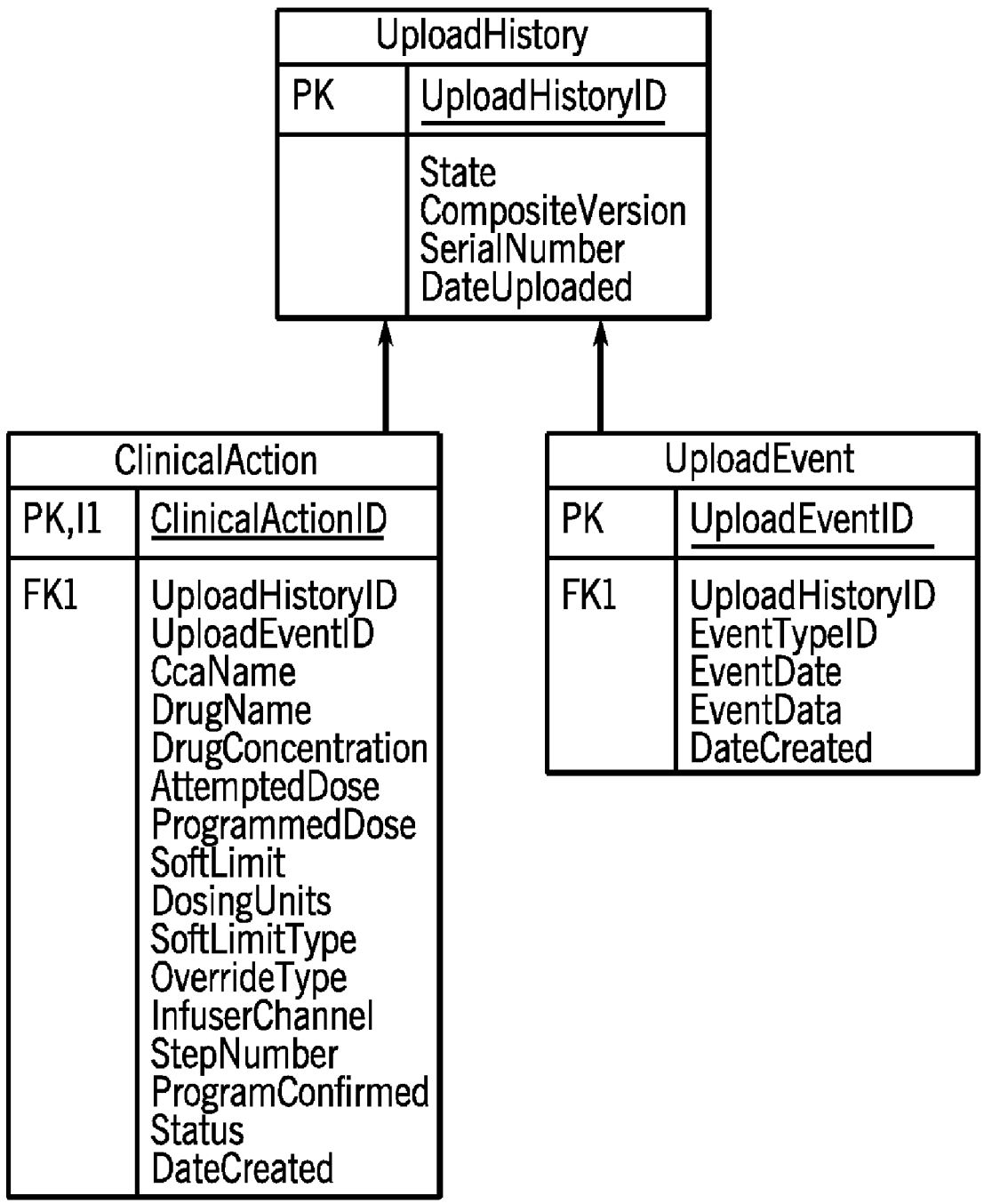
FIG. 26 is a diagram illustrates a data model to support a soft limit alert or override clinical event.

In one example, all of the fields listed are required and are constrained to be "not null". In this example, all data fields support a value of "not available" to indicate that a specific field has no value because it could not be retrieved from the event log (e.g. due to overwriting when the log exceeds 321 lines). The following diagram illustrates the data model to support the Soft Limit Alert or Override clinical event. FIG. 26 is a diagram illustrates a data model to support a soft limit alert or override clinical event.

FIG. 7 shows an example of one soft limit override report. FIG. 7A contains an explanation of the headings and data shown in FIG. 7. FIGS. 7B-E and 8A-D show examples of soft and hard limit override reports for several different drugs, in this example, dopamine, heparin, insulin, and Vancomycin. The reports shown in FIGS. 7B-7E list the type of alert presented (lower hard limit, lower soft limit, upper soft limit, upper hard limit) and the number of times each alert was presented. For each type of alert presented, the report also shows statistics relating to how the user responded to the alerts. In this example, the report indicates the number of times the alert was overridden or not overridden. In addition, the report also indicates the number of times "No" was entered by a user when asked to confirm the entry of information. FIGS. 8A-8D show another example of alert and override reports. The reports shown in FIGS. 8A-8D are similar the reports shown in FIGS. 7B-7E, except each alert is separated by CCA (in this example, ICU and MedSurg). It is apparent from these examples that any desired information can be collected and reported by the present invention.

One advantage of the present invention is that both hard and soft limits can be provided for each drug, and any drug/CCA combination can be ascribed one, two, three, or four limits. When the capability of providing both hard and soft limits exists, there the sixteen combinations of limits that can be used. Each of the four limits can contain a value specifying a limit, or the "limit" can be unrestricted (indicated by None in the appropriate field). These two possibilities exist for each limit, i.e., the lower hard limit, lower soft limit, upper soft limit and upper hard limit). This feature allows a user to configure a device in various combinations, such as a hard upper limit only, hard and soft upper and lower limits, hard and soft upper limits (no lower limits), hard and soft lower limits (no upper limits), etc. In the example of two sets of upper and lower limits, there are 16 possible combinations of configurations. If additional sets of limits are used, more combinations are possible. In one embodiment, hard limits are the upper and/or lower dose limits for the selected drug and selected CCA that cannot be overridden by a user. The hard limit in another embodiment may require or allow supervisory override. The hard limits, authority levels, and overridability, are defined by a hospital for each drug in its drug library. The hard limits for a particular drug may vary across different CCAs, if assigned.

In one embodiment, soft limits are upper and/or lower dose limits for the selected drug and selected CCA that can be overridden by a user. Soft limits for a particular drug, if assigned, may vary across CCAs. A set of rules is provided for the drug library that triggers alerts or warnings when soft limits are reached. The warnings require an explicit override step on the part of the operator. Similarly a set of rules is provided for the drug library that provide hard limits on the range of delivery rates the user is allowed to program. For example, if a lower soft limit is set to 10 mL/hr and the clinician enters 9 mL/hr, the infuser will display a soft limit override alert. This alert, which is recorded in the infuser's history log, notifies the clinician that the entry is outside the range of the soft limits set for that drug entry. The clinician can choose to continue programming using the override, or cancel the override and re-enter another value. If the clinician chooses to override the soft limit, the event is recorded separately in the infuser's history log. Hard and soft limits can be set on various other drug parameters. Examples include a dosage rates, drug delivery time, drug concentration, the weight of a patient, the volume to be infused (VTBI), etc.

Another use of hard and/or soft limits relates to correct data entry. For example, a hard limit can be set on time period entries so that a user can only enter values between 0 and 59. In this example, the system will realize a data entry error and force the user to enter a value in the valid range. In another example, for various drug fields, only certain values or ranges will be allowed to be entered. 15A shows examples of values that may be entered for drug unit, drug amount, diluent amount, delivery dose/rate units, and hard and soft limit fields. If a user attempts to enter other values, the system will force the user to enter a valid field, or will generate an alert or alarm.

The invention also allows the import and export of drug libraries from one computer to another. Before a library can be imported, it must be exported. Generally, a drug library can be exported to a finalized drug Library (FDL) having a pre-defined format, which makes the library safely and securely portable to other computers where they can be imported and set as an active library. For example, for a first PC having an active library, the library can be exported into a binary format, and moved (via a network, computer readable media, etc.) to a second PC, where it is imported, therefore synchronizing the libraries at the first and second PCs. The special file extension (FDL) and recognition by the software between computers is required.

When an FDL is exported, the entire drug library is first "selected" from the database, using the SelectEntireDrugLibrary stored procedure (see below). That procedure actually contains several select statements, with one statement per table. The tables are the same as for copy. For each table, the export method serializes the table name, number of rows and columns, then each row is serialized, column by column. Note that the original database index values are serialized. When the library is read from the file, the index values will no longer be valid—but should be mapped, the same as if the library were being copied. In one example, the FDL Files are "read only" files. Since the FDL files are in Java-serialized format, a FDL file is not easily modified by a user with ordinary software applications. This feature is part of the reason for using serialization—to discourage users from tampering with finalized drug libraries.

When an FDL is imported, first all the serialized information is read into memory, in the form of a three-dimensional array. There are three array dimensions, one dimension for the tables, one dimension for the rows, and one dimension for the columns. The sizes of the row and column dimensions may be different for each table. This "raw" data is inserted into the database, table-by-table, row-by-row. Also, index mappings may be performed along the way. Next, as the rows are inserted, new index values will be generated, and are stored in a map, similar to what happens during the copy operation. Some tables may contain indexes to other, previously inserted tables. These indexes are converted from the original values to the new values, using the generated map. These converted index values are the ones that are inserted into the new rows. After an FDL has been stored in the database, it becomes the Finalized Drug Library, making another Finalized Drug Library into an Archived library.

Following is a description of FDLData.java, which lets the FDL import know which order the tables are stored in the array, what the index dependencies are, which columns to store in the map, which column values need to be mapped to new values before they can be inserted, etc.

It is important to realize that, just as with copying a drug library, the order in which tables are processed during an FDL import is important. That order is encoded in the FDLData.java file as enumerated constants. Following is an example of such enumerated constants:

```
public static final int DRUG_LIBRARY_TABLE =      1;
public static final int DOSING_UNITS_TABLE =      2;
public static final int DRUG_AMOUNTS_TABLE =      3;
public static final int DILUENT_UNITS_TABLE =     4;
public static final int DRUG_LABELS_TABLE =       5;
public static final int DRUG_CLASS_TABLE =        6;
public static final int DRUGS_TABLE =             7;
public static final int CONCENTRATION_TABLE =     8;
public static final int RULE_SET_TABLE =          9;
public static final int CCA_TABLE =              10;
public static final int DEVICE_SETTINGS_TABLE =  11;
public static final int CCA_SETTINGS_TABLE =     12;
public static final int INFUSER_SETTINGS_TABLE = 13;
public static final int DRUG_FORMULARY_TABLE =   14;
public static final int CCA_LIBRARY_TABLE =      15;
public static final int TABLE_COUNT =            16;
```

These constants can be used as indexes into the three-dimensional array of raw data described above. This section of code may also be generated by the PostSchemaChange.sql file, in case changes have been made to the database schema.

For each table that gets exported/imported there is an instance of TableInfo, which keeps track of the table name, the number of columns, which of its columns, if any, other tables might depend on (the idColumn), and finally, a set of indexes to tables that this table depends on. The "idColumn", if specified, is generated by the database for each row of that table, as the rows are inserted. The old value (from the serialized file) and the new value (from the database row insertion) are stored in an index map. Then, every other in-memory table that references the old index is updated to contain the new index before its rows are inserted. For example, the "idColumn" of the RuleSet table shown below is its RuleSetID column, which happens to be the 2nd column in the TableInfo table. Thus, the "idColumn" in the TableInfo instance for RuleSet equals 1 (the first column is 0, the 2nd column is 1, . . . ). Now, assume that when the FDL was exported, there was a row in the RuleSet table where the RuleSetID was equal to 5047:

| RuleSet (slightly simplified): | | | | | | | |
|---|---|---|---|---|---|---|---|
| RuleSetID | DrugLibraryID | DrugLabelID | DosingUnitID | LHL | LSL | USL | UHL |
| ... | ... | ... | ... | ... | ... | ... | ... |
| 5047 | 1038 | 2 | 0 | None | 10 | 200 | None |
| ... | ... | ... | ... | ... | ... | ... | ... |

The CcaLibrary and DrugFormulary tables (shown below) each have a RuleSet dependency—their RuleSetID columns

| CcaLibrary (slightly simplified): | | | | | |
|---|---|---|---|---|---|
| CcaLibraryID | DrugLibraryID | RuleSetID | CcaID | DrugFormularyID | DisplayOrder |
| ... | ... | ... | ... | ... | ... |
| 3252 | 1038 | 5047 | 2108 | 4217 | 0 |
| ... | ... | ... | ... | ... | ... |

| Drug Formulary: | | | |
|---|---|---|---|
| DrugFormularyID | DrugLibraryID | ConcentrationID | RuleSetID |
| ... | ... | ... | ... |
| 4217 | 1038 | 6150 | 5047 |
| ... | ... | ... | ... |

Now assume that when the FDL is imported, that particular row of the RuleSet table (shown below) is given a new index value of 5122.

| RuleSet (slightly simplified): | | | | | | | |
|---|---|---|---|---|---|---|---|
| RuleSetID | DrugLibraryID | DrugLabelID | DosingUnitID | LHL | LSL | USL | UHL |
| ... | ... | ... | ... | ... | ... | ... | ... |
| 5047 | 1038 | 2 | 0 | None | 10 | 200 | None |
| ... | ... | ... | ... | ... | ... | ... | ... |
| 5122 | 1039 | 2 | 0 | None | 10 | 200 | None |

Later, before the CcaLibrary or DrugFormulary tables are inserted, any RuleSetID values of 5047 are first changed to 5122. The "idColumn" setting of 1 tells the FDL import code to store the 5047 to 5122 mapping.

| Mapping (in memory, not a database table): | |
|---|---|
| OldIndexValue | NewIndexValue |
| ... | ... |
| 5047 | 5122 |
| ... | ... |

The 5047 values in the CcaLibrary and DrugFormulary tables are changed to 5122 while they are still in memory—in the three dimensional table of raw data. After those tables have been processed, the CcaLibrary and DrugFormularyID tables are shown below.

| CcaLibrary (slightly simplified): | | | | | |
|---|---|---|---|---|---|
| CcaLibraryID | DrugLibraryID | RuleSetID | CcaID | DrugFormularyID | DisplayOrder |
| ... | ... | ... | ... | ... | ... |
| 3252 | 1038 | 5047 | 2108 | 4217 | 0 |
| ... | ... | ... | ... | ... | ... |
| 3333 | 1039 | 5122 | 2222 | 4444 | 0 |
| ... | ... | ... | ... | ... | ... |

| Drug Formulary: | | | |
|---|---|---|---|
| DrugFormularyID | DrugLibraryID | ConcentrationID | RuleSetID |
| ... | ... | ... | ... |
| 4217 | 1038 | 6150 | 5047 |
| ... | ... | ... | ... |
| 4444 | 1039 | 6666 | 5122 |
| ... | ... | ... | ... |

Referring back to the FDLData.java file, various sections of the file are automatically generated by the PostSchemaChange.sql file. They can be cut and pasted from the output of that file into the java code. Specifically, the table order constants (as shown above), and the TableInfo array and its contents can be generated in the event of a database schema change.

The PostSchemaChange.sql file also generates most of the SelectEntireDrugLibrary stored procedure (described below) at the same time. Again, the SQL code it generates can be cut and pasted into the proper place in the SelectEntireDrugLibrary.sql file.

When a FDL is to be exported, the data that makes up the library is obtained from the database (so it can be serialized to a file). The SelectEntireDrugLibrary stored procedure does that. The procedure utilizes several select statements, selecting the tables in a specific order, and selecting the columns of any given table in a specific order.

Since the order of the tables, and the order of the columns within those tables is important to the FDL import code that reconstructs a drug library, it is essential that the FDL export, FDL import, and SelectEntireDrugLibrary code be kept in sync with each other. The slightest change in the database schema can necessitate changes in FDLData.java and SelectEntireDrugLibrary, as well as the CopyDrugLibrary stored procedure. The slightest error (mismatch) will stop things from working properly.

Except for the CopyDrugLibrary code, most of the java and SQL changes can be produced by running the PostSchemaChange.sql file after the new schema is in place. Simply cut and paste the generated code over the matching/similar code in those files. The CopyDrugLibrary code changes can also be automated.

One feature of the present invention is that data can be imported to and exported from the system. Library text files that use either Comma Separated Values (CSV) or Tab Separated Values (TSV) can be imported by the system. One unique feature is the entire file must pass the RSV checks specified above or the entire import is considered invalid.

It will be appreciated by one skilled in the art that the present invention is applicable to a variety of pumps or medical devices and not limited to the pumps with which it is described herein. Furthermore, one skilled in the art will appreciate that the connections between the pumps and the computer could be wireless or hard-wired, without detracting from the invention. Wireless communication engines can be connected to the pump and the computer and use a wireless network utilizing communication protocols such as BLUETOOTH™ (IEEE 802.15) or other protocols such as those described in IEEE 802.11, 802.11a, 802.11b, and 802.11g. Communication within the wireless network may utilize radio frequency electromagnetic radiation, infrared radiation, or other means for accomplishing wireless communication between network elements.

In one example, the plug and play module 4 can house or encase a wireless communication or connectivity engine. Conventional wireless communication modules for medical pumps have been of the external plug-in, bolt-on type for optimal reception and transmission. These conventional communications modules add significantly to the space required for the pump and alter its profile. They can be damaged or dislodged if the pump is dropped. Furthermore, there are stringent standards for maximum electrical emissions from medical equipment to prevent potential interference with other medical equipment. The wireless plug and play module 4 of the present invention does not substantially increase the space occupied by the pump. With the improved antenna design described below, placing the plug and play module 4 inside the pump housing 2 still provides good position/orientation tolerant reception and transmission characteristics and provides the surprising result of lower, better controlled electronic emissions from the device.

As mentioned above, an infusion pump of the present invention is capable of being connected to various other devices. In one example, the present invention uses a connectivity engine to provide system functions, in addition to enabling a pump to connect to a variety of other devices. Following is one example of a connectivity engine which can be used with the present invention. In the example described, the various features and capabilities can be customized as desired.

The connectivity engine is an assembly inside the housing of an infuser with the purpose of providing key system functions and enabling the infuser to connect to a variety of external systems including medication management units (MMU), hospital information systems (HIS), pharmacy information system (PhIS), and other medical information systems through both wired and wireless communication links. The connectivity engine can interface via data and address buses on its printed wiring assembly to the CPU printed wiring assembly via a board to board connector. In one example, the connectivity engine supports about 1-2 Mbytes of read-only program and 1 M-byte or more of read/write data memories for the infuser CPU printed wiring assembly. The connectivity engine can communicate with a host computer via a serial data port, which is externally located on the rear of the infuser unit. In one example, the data port is electrically isolated.

In this example, the connectivity engine includes a front panel lockout switch, which is externally accessible on the rear of the unit. The connectivity engine may also include a nurse call interface, which is externally located on the rear of the unit. The nurse call interface allows use with a nurse call device, such as a switch held by a patient that allows the patient to send an alarm message to a nurse. The connectivity engine may also include an alarm volume control, which is accessible from the rear of the instrument. This control will adjust the volume level for an audible alarm to alert the user to errors, warnings, etc.

The connectivity engine is a modular and intelligent printed wiring assembly capable of supporting the interconnection of an infuser with a variety of external systems for the purpose of establishing bi-directional communications between the infuser and external systems. Examples of external systems may include medication management units (MMU), medical information systems, HIS, and external wireless Access Points. Other examples of external systems include one or more PCs for downloading drug libraries and software to the infuser and uploading logs from the infuser.

As mentioned above, the present invention is capable of both wired and wireless communications. Examples of wired interfaces that may be supported include Ethernet 10BaseT and 100BaseT standard, as well as Megabit and fiber optic interfaces. Examples of wireless interfaces that may be supported include IEEE802.11a/b/g, as well as any other desired interfaces. The connectivity engine can support various network protocols, including XML, HTML, ftp, and Telnet services.

In one example, the present invention normally operates using either a wired or wireless interface. In another example, the invention can simultaneously use both wired and wireless interfaces. In this example, when a fault is detected in either mode, all communications automatically can switch to the working mode.

The connectivity engine hardware can take on many forms, depending on the functionality and capabilities desired. In one example, the connectivity engine includes the following sub-circuits: CPU memory—RAM and flash, external serial interface, nurse call interface, audio volume control, lockout switch, connectivity engine controller, Ethernet interface, wireless interface, and antenna assembly. The following external connectors can also be included: Ethernet RJ-45 connector, RF connector for connecting the Wi-Fi transceiver to the Antenna printed wiring assembly, RS232 serial port DB9 connector, and Nurse Call Interface connector.

Figure 9:
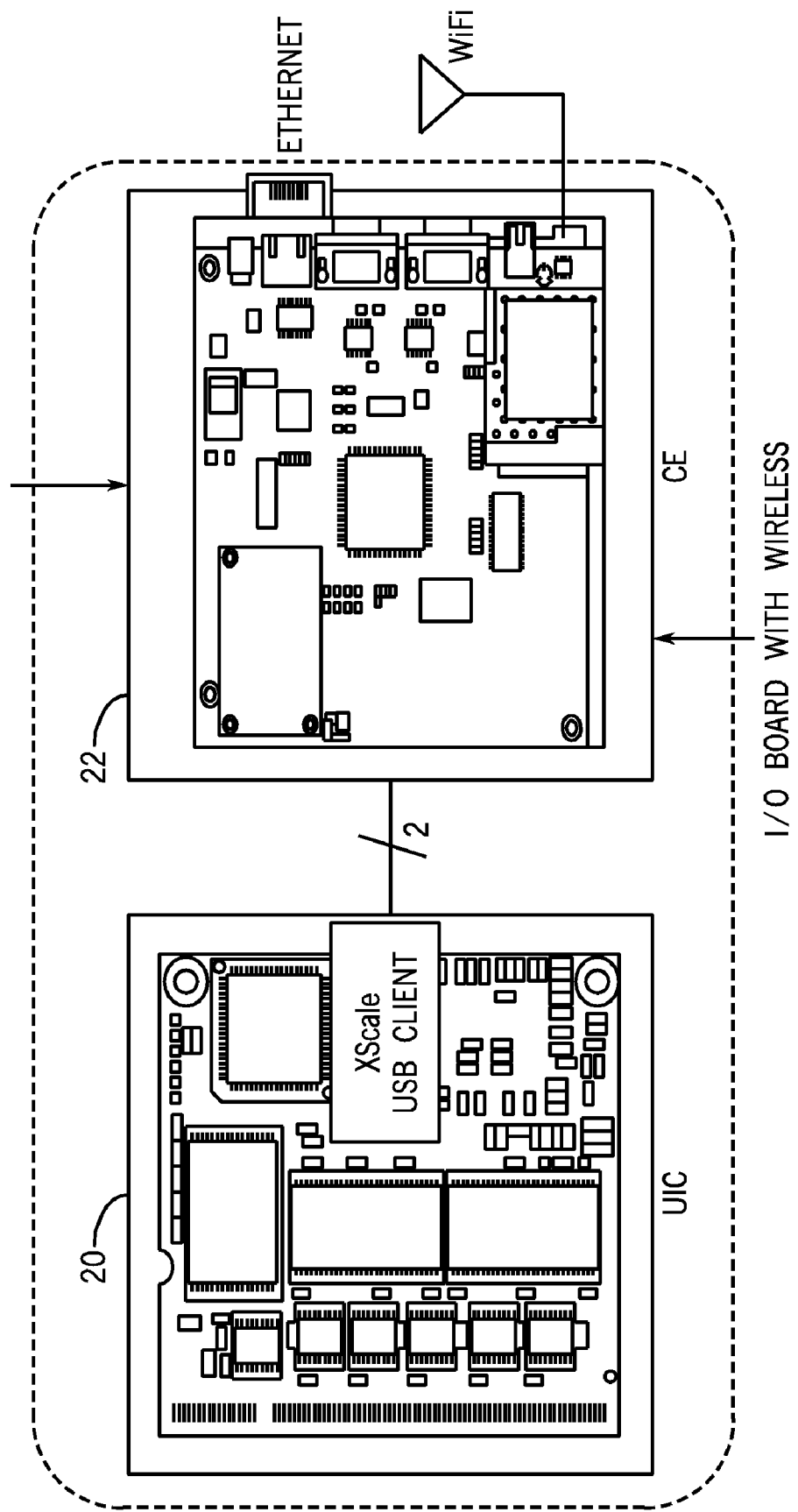
FIGS. 9-11 are block diagrams of exemplary connectivity that may be used with the present invention.
Figure 10:
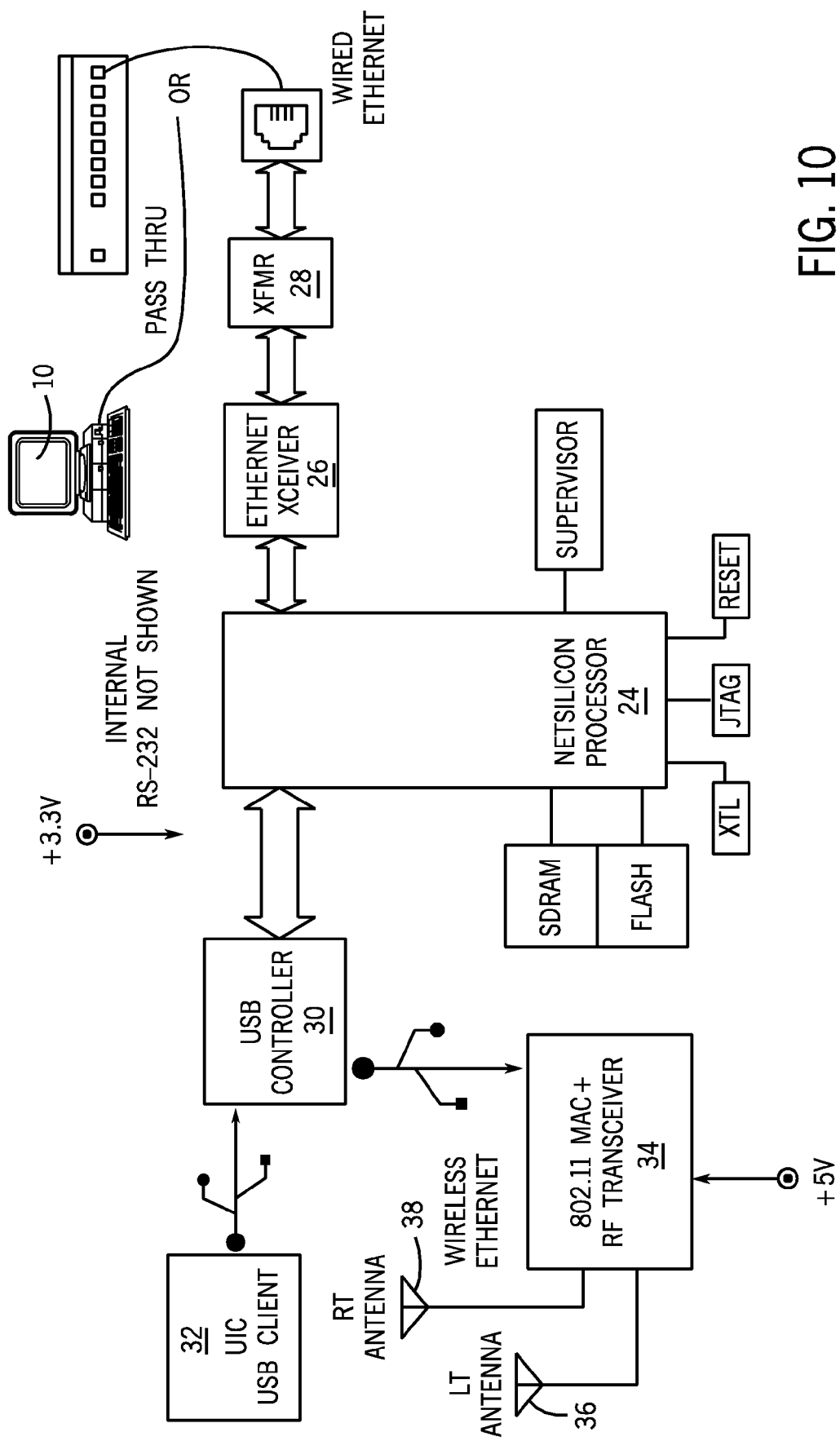
Figure 11:
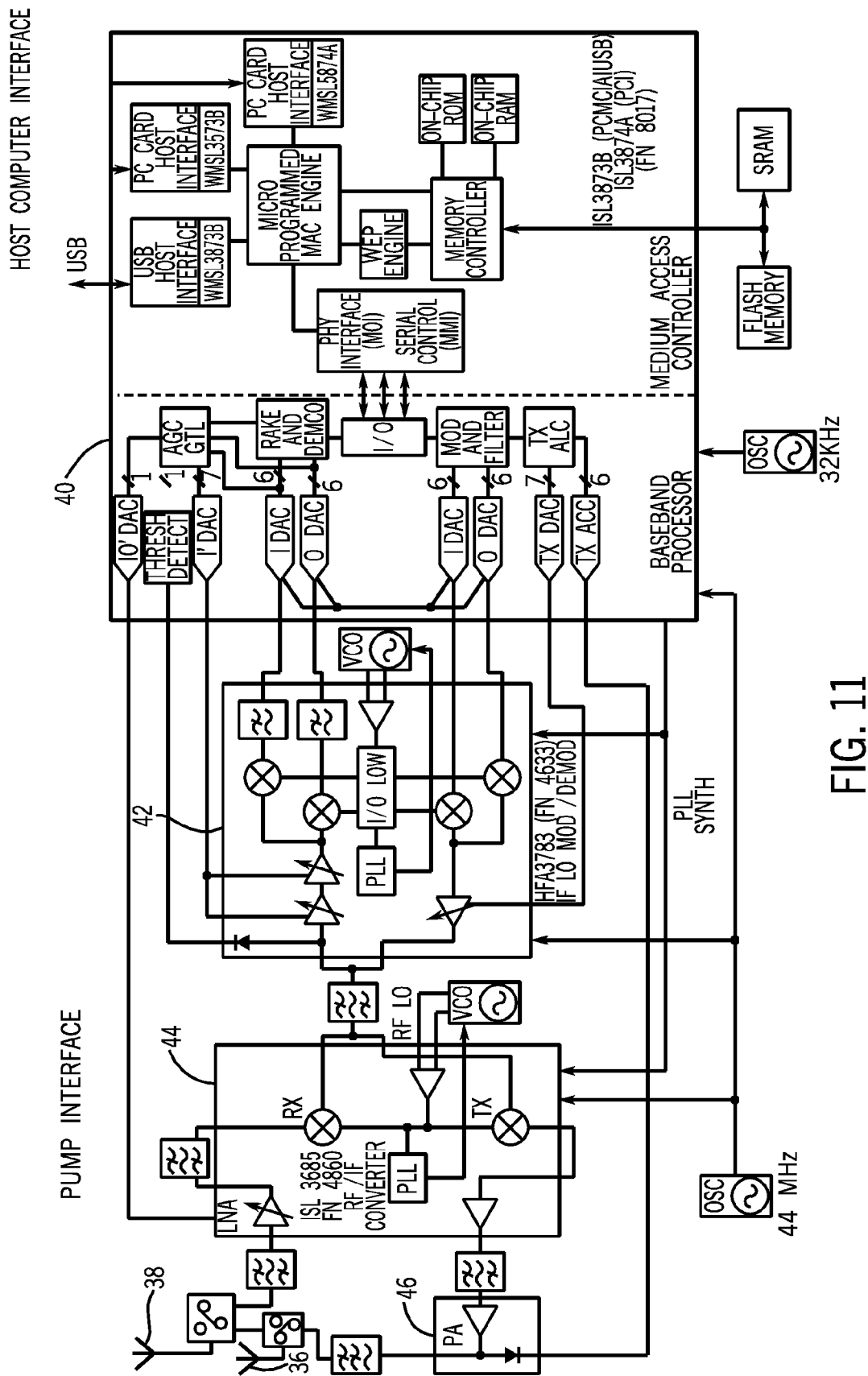
Figure 12A:
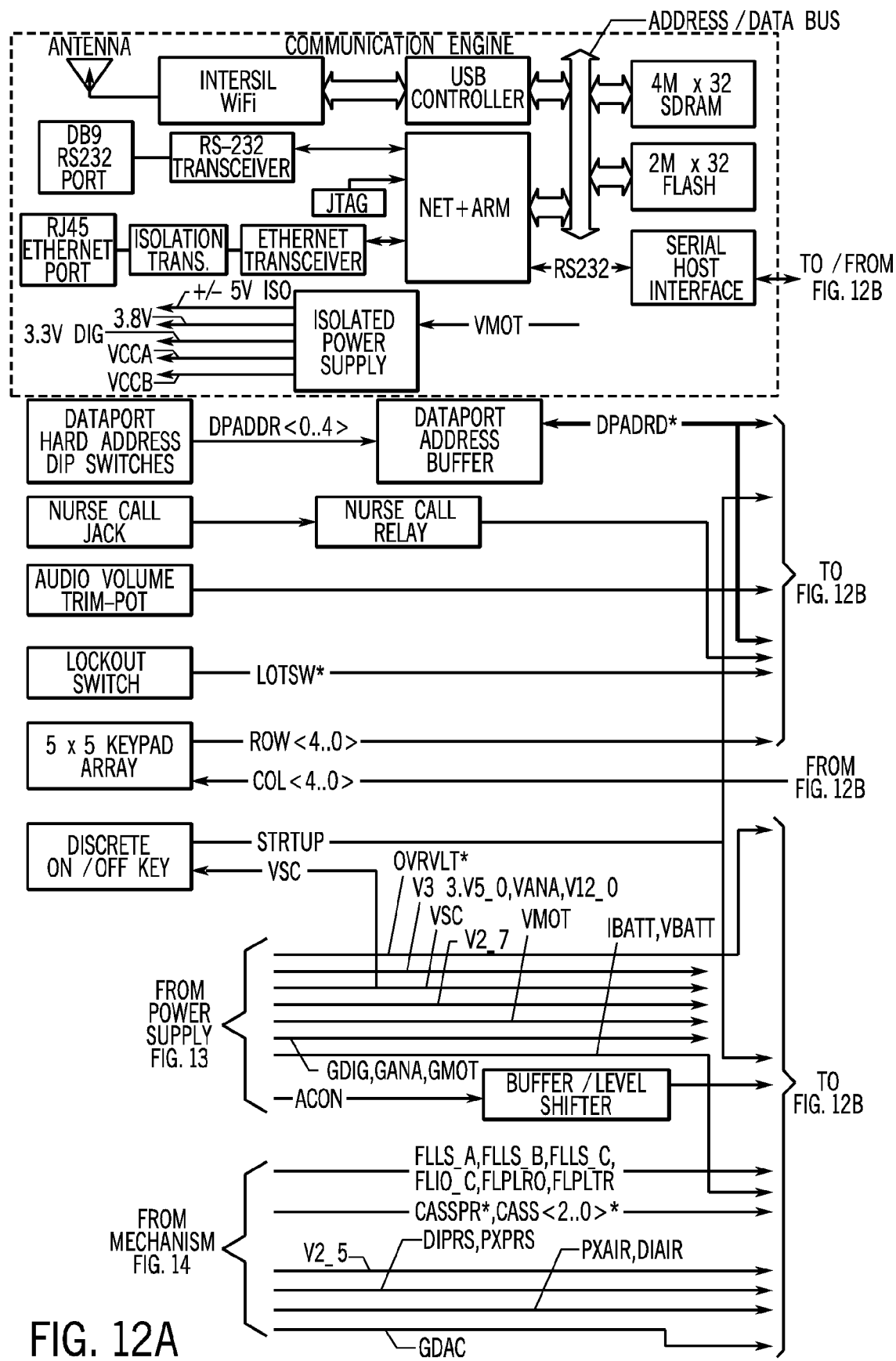
FIGS. 12A-14 are block diagrams of one example of an electronics system for use with the present invention.
Figure 12B:
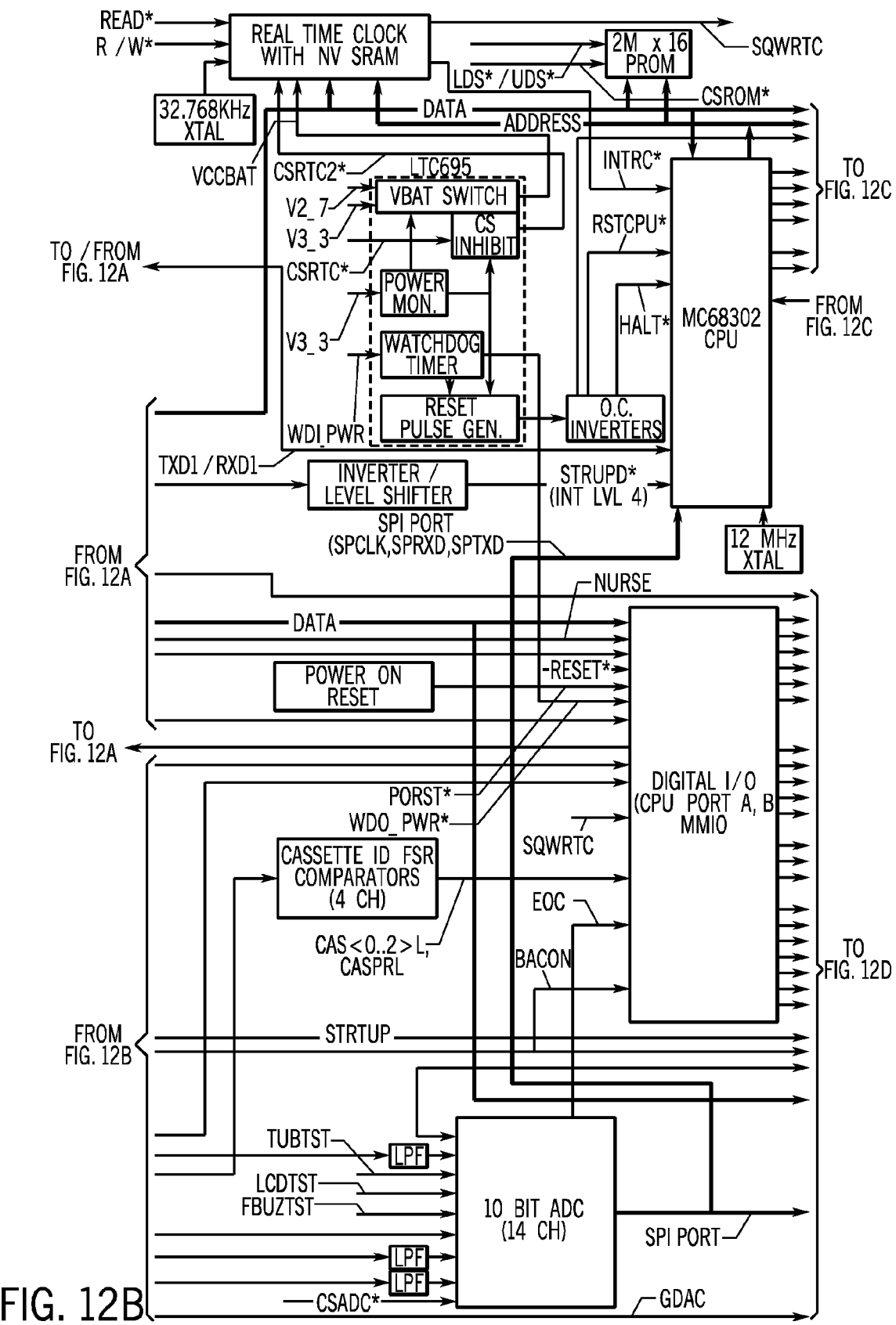
Figure 12C:
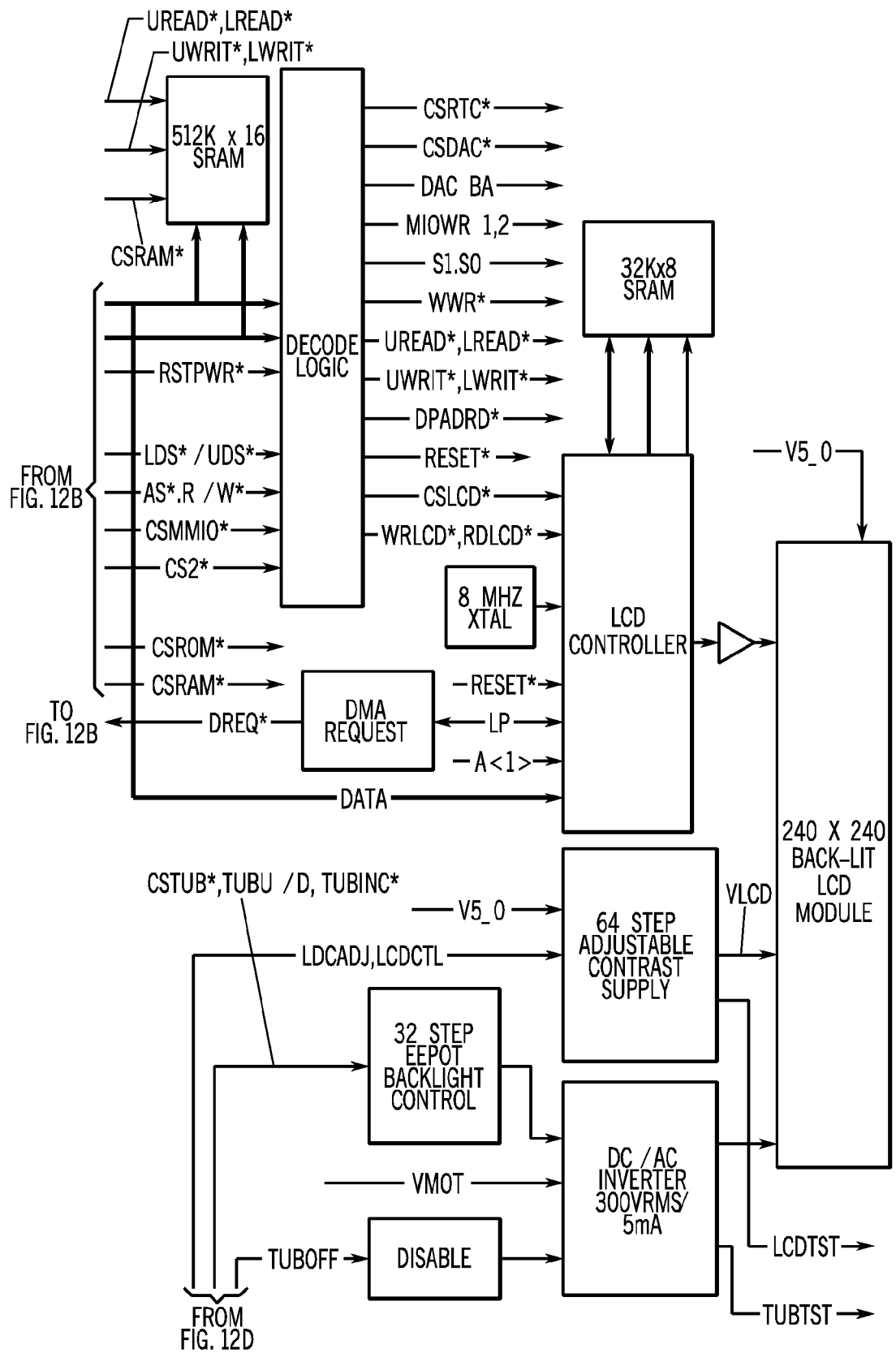
Figure 12D:
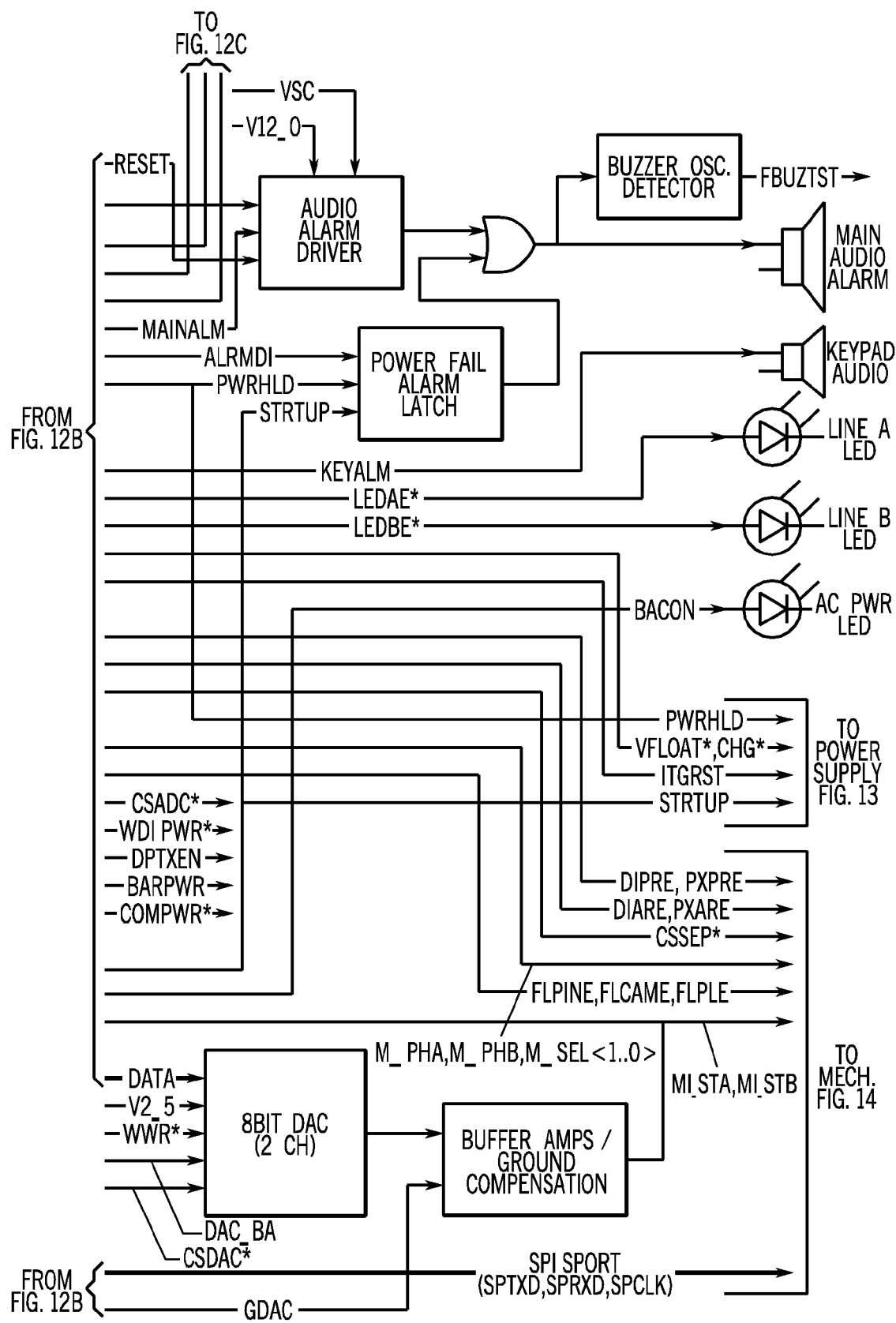

FIGS. 9-11 are block diagrams of an exemplary connectivity engine that may be used with the present invention and fully enclosed within the pump housing rather than in a removable plug and play module. FIG. 9 shows a user interface controller (UIC) 20, which is connected to a connectivity engine 22 via a universal serial bus (USB). Of course, other interfaces could also be used (e.g., RS232 serial interface, parallel interface, etc.). The connectivity engine 22 is an input/output board shown in FIG. 9 with Ethernet and WiFi connections. FIG. 10 is a block diagram of a connectivity engine including a processor 24. The processor 24 is connected to an Ethernet transceiver 26 and transformer 28 to provide an Ethernet interface to communicate with one or more PCs 10. This interface could also be provided wirelessly. The processor is also connected to a USB controller 30. The USB controller 30 is connected over a USB interface to UIC USB client 32 and to RF transceiver 34.

The RF transceiver 34 is shown with two antennas 36 and 38. While the present invention may include just one antenna, two antennas can improve the performance of the invention. Since the communication between the invention and other devices can be critical, it is desirable to provide the most reliable wireless connection possible. Two diverse antennas optimize the wireless communication coverage of the invention. The invention uses a combination of two different diversity schemes, spatial diversity and pattern diversity. Traditionally, in spatial diversity two identical antennas are located at two separate locations to provide diversity reception to a common receiver. In this case, the scheme not only separates the antennas physically but also achieves pattern diversity by placing the two antennas orthogonally. This way, peaks in one antenna fill out the nulls of the other antenna such that that combined radiation pattern looks more omnidirectional than just a single antenna. The antenna diversity scheme achieves several objectives. First, it is desirable to have the antenna(s) not so apparent externally, making it desirable to use an internally embedded antenna(s). Second, in most applications, the invention must meet the EMC requirements specified in the IEC 60601-1-2, 2nd Edition standard, which limits the amount of emissions a device can emit. The use of two diverse antennas helps to achieve these objectives. In one example, the antenna(s) used with the present invention are enclosed within the housing of the infusion pump. This help to keep dirt, harmful solvents and debris away from the antennas, enhances control of emissions, as well as reduces the chance of damage to an antenna.

In another example, the connectivity engine includes memory used as cache for temporarily storing information. The cache can make the system work more efficiently and more reliably.

FIG. 11 is a block diagram of the wireless interface shown in FIG. 10 and shows a baseband processor and medium access controller 40, which includes a USB interface for communication with a host computer. The processor 40 is connected to a modulator/demodulator 42, an RF/IF converter 44, and a power amplifier 46. The antennas 36 and 38 are driven by the power amplifier 46 and the RF/IF converter 44.

Figure 13:
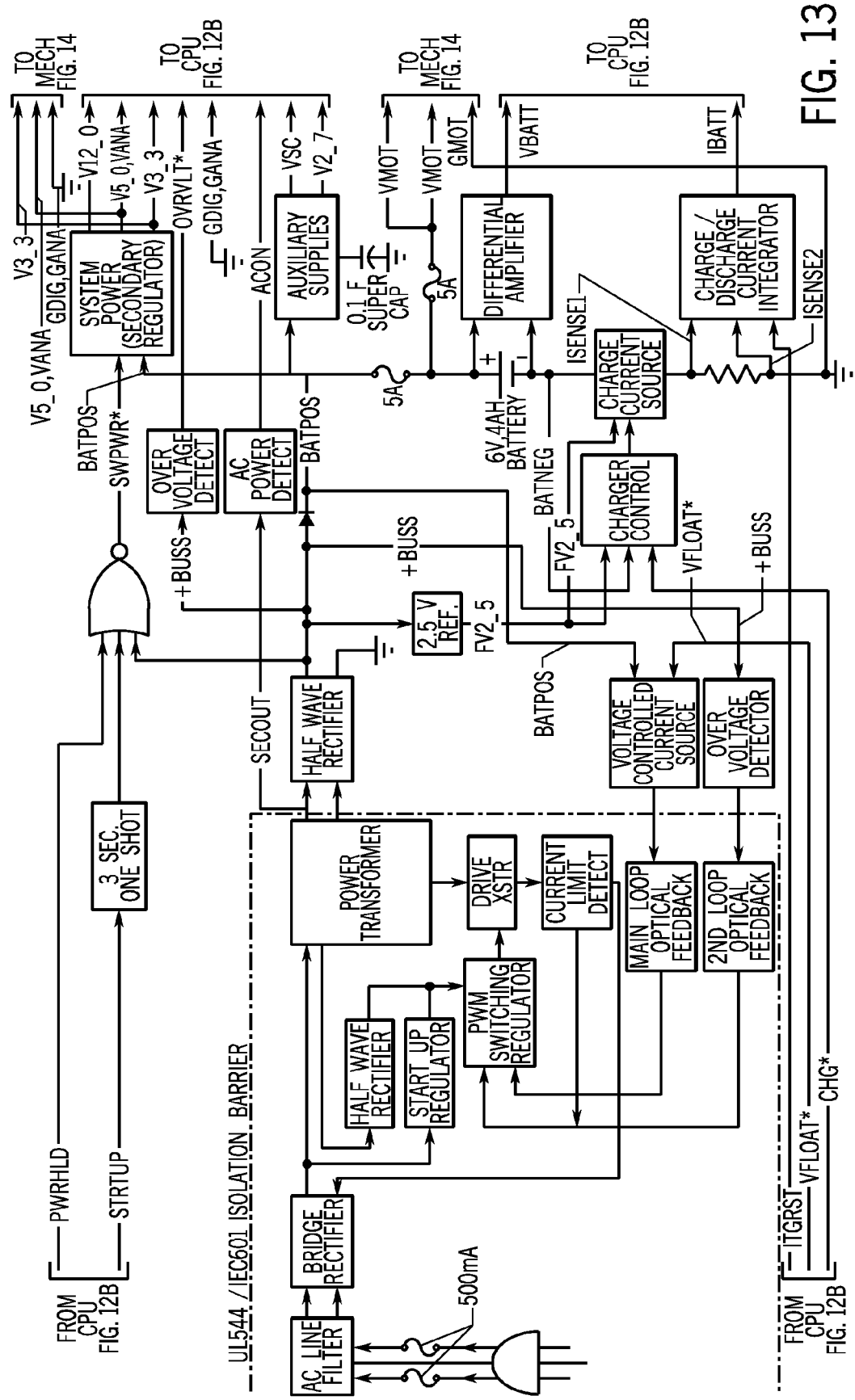
Figure 14:
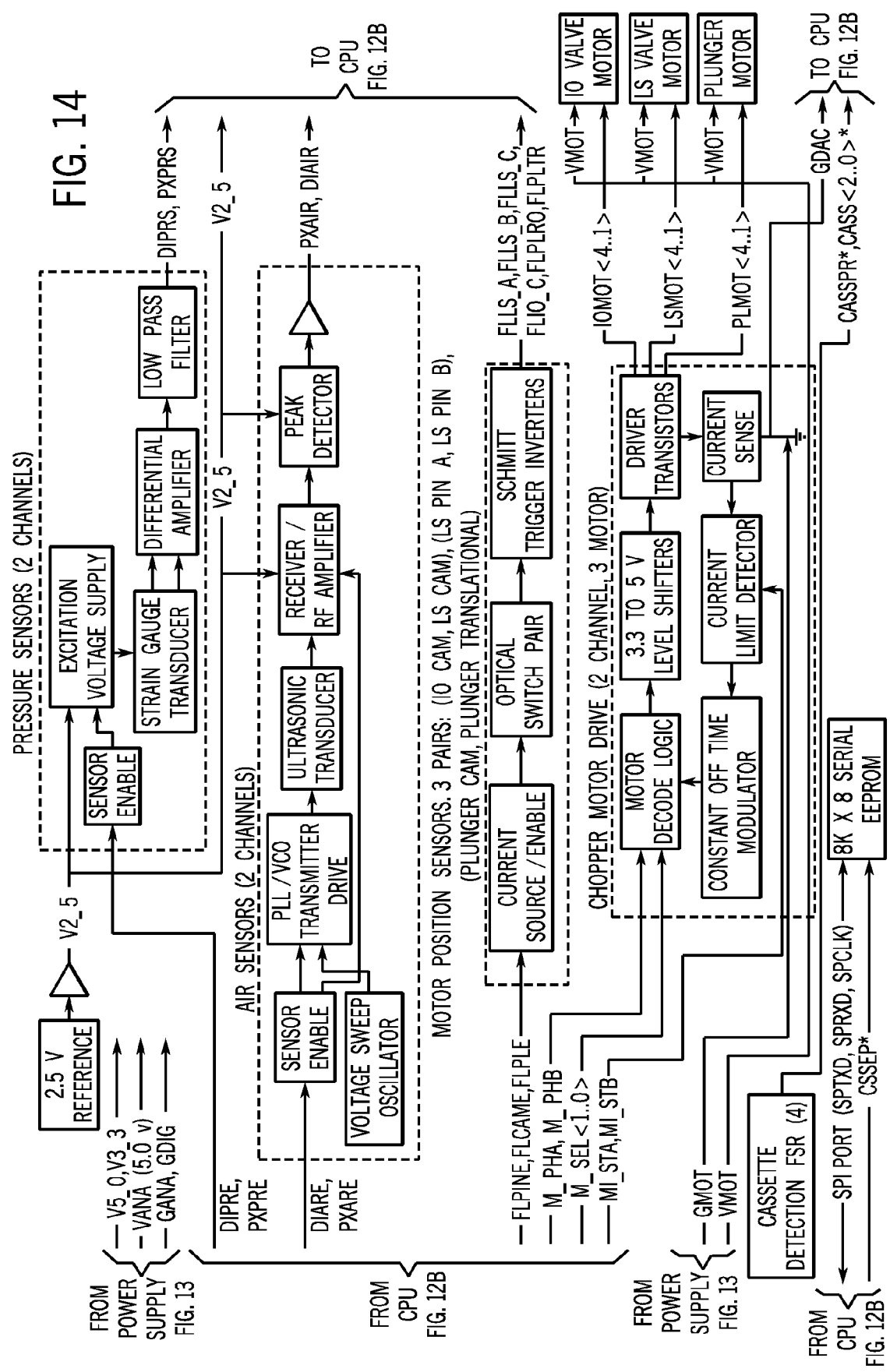

FIGS. 12A-15 are electronics system diagrams of one example of the present invention, as applied to the Abbott PLUM A+® Infuser. FIGS. 12A-12D shows a CPU and a communication or connectivity engine. The communication engine facilitates communication with other devices via wired or wireless interfaces. The communication engine can utilize the same orthogonally arranged antennas as described above relative to FIGS. 9-11. FIG. 12 also shows a digital I/O chip for interfacing with various components, such as switches and user controls, a nurse call jack, keypads, alarm speakers, LEDs, etc. FIG. 13 shows the power supply subsystem, including power supply circuitry and an isolation bather. FIG. 14 shows the mechanism subsystem, including pressure sensors, air sensors, motor position sensors, and a motor drive.

Figure 17A:
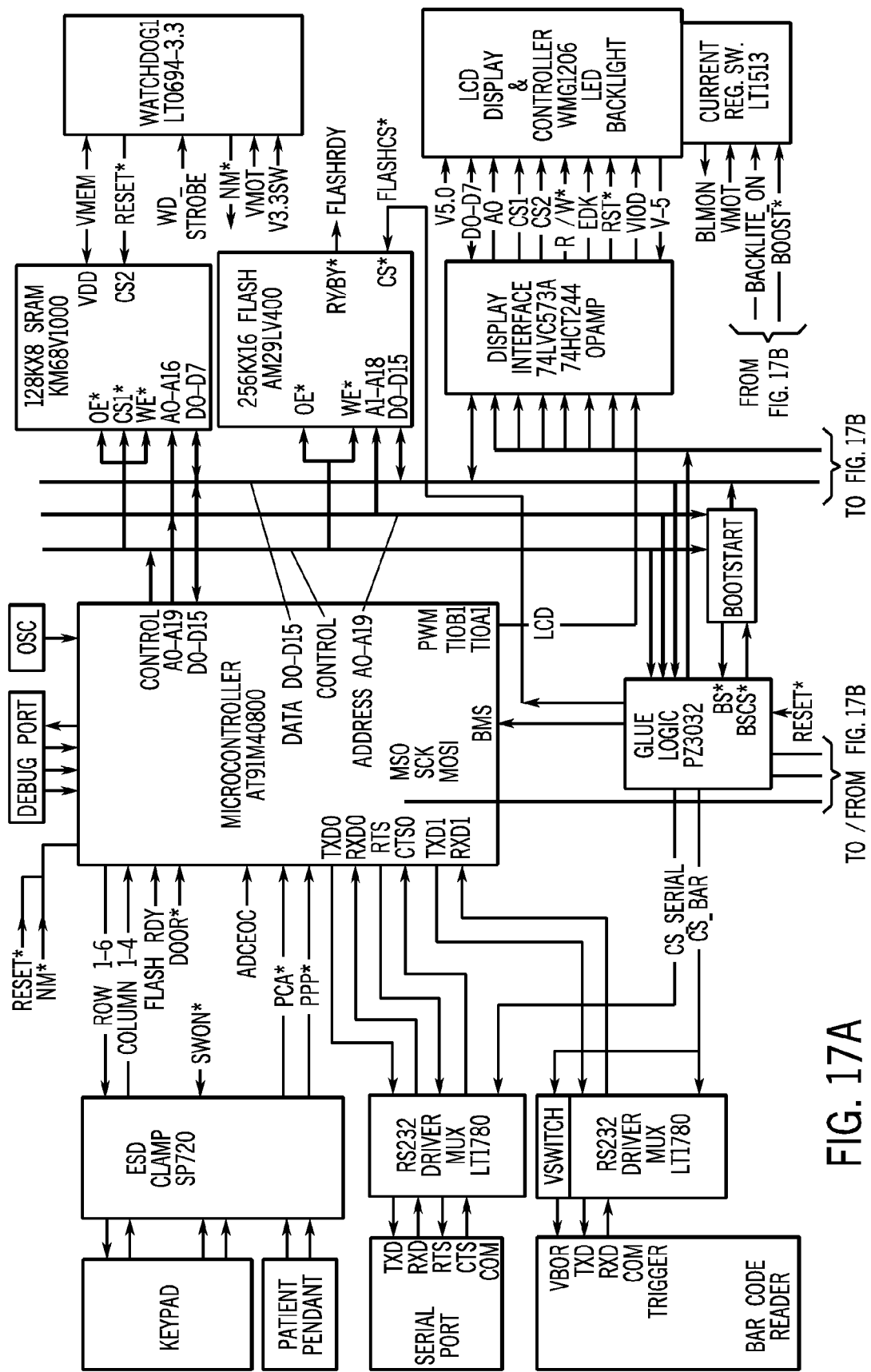
FIG. 17-19 are block diagrams showing a patient controlled analgesia pump with a wireless connectivity or communication engine according to the present invention.
Figure 17B:
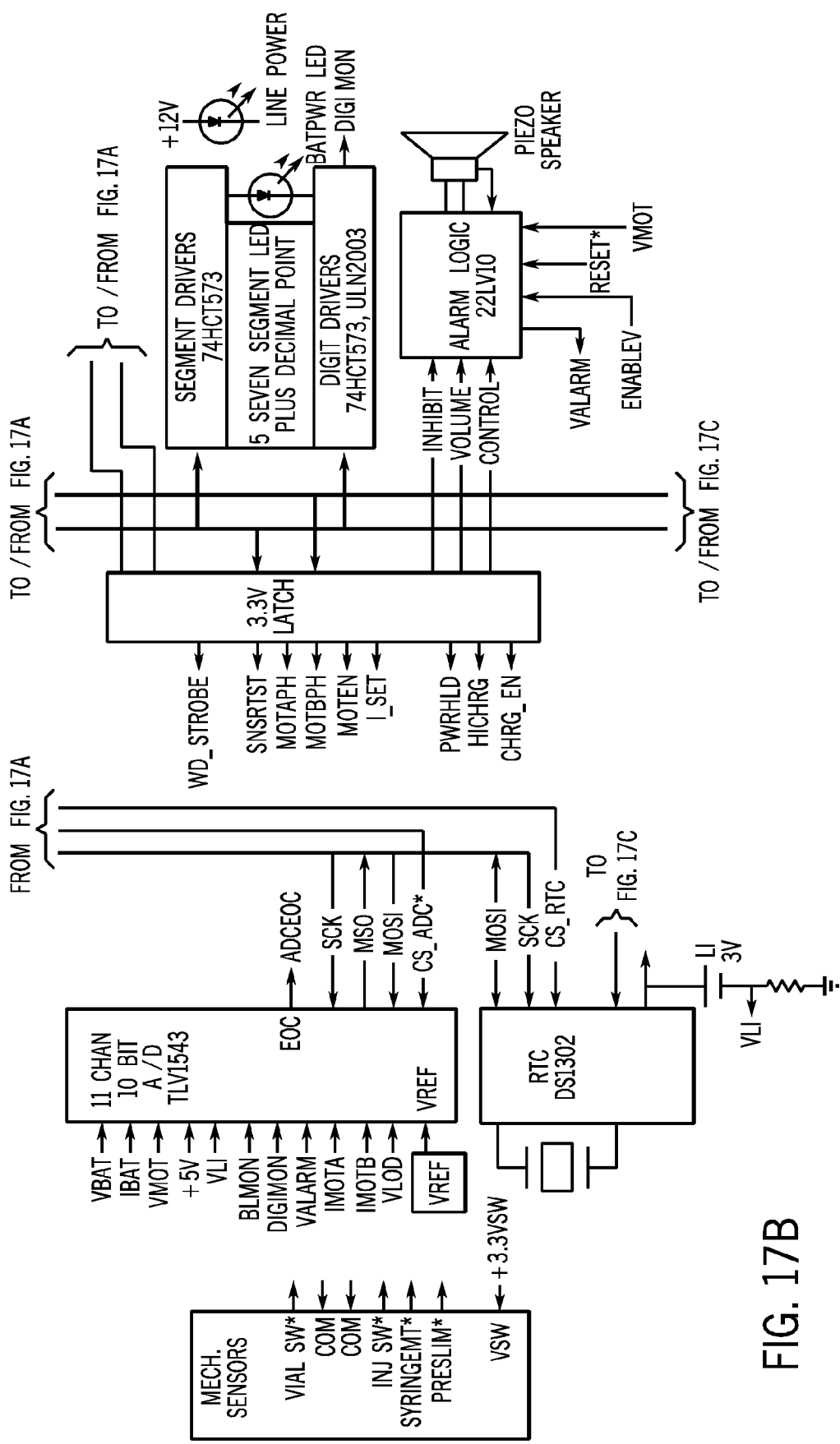
Figure 17C:
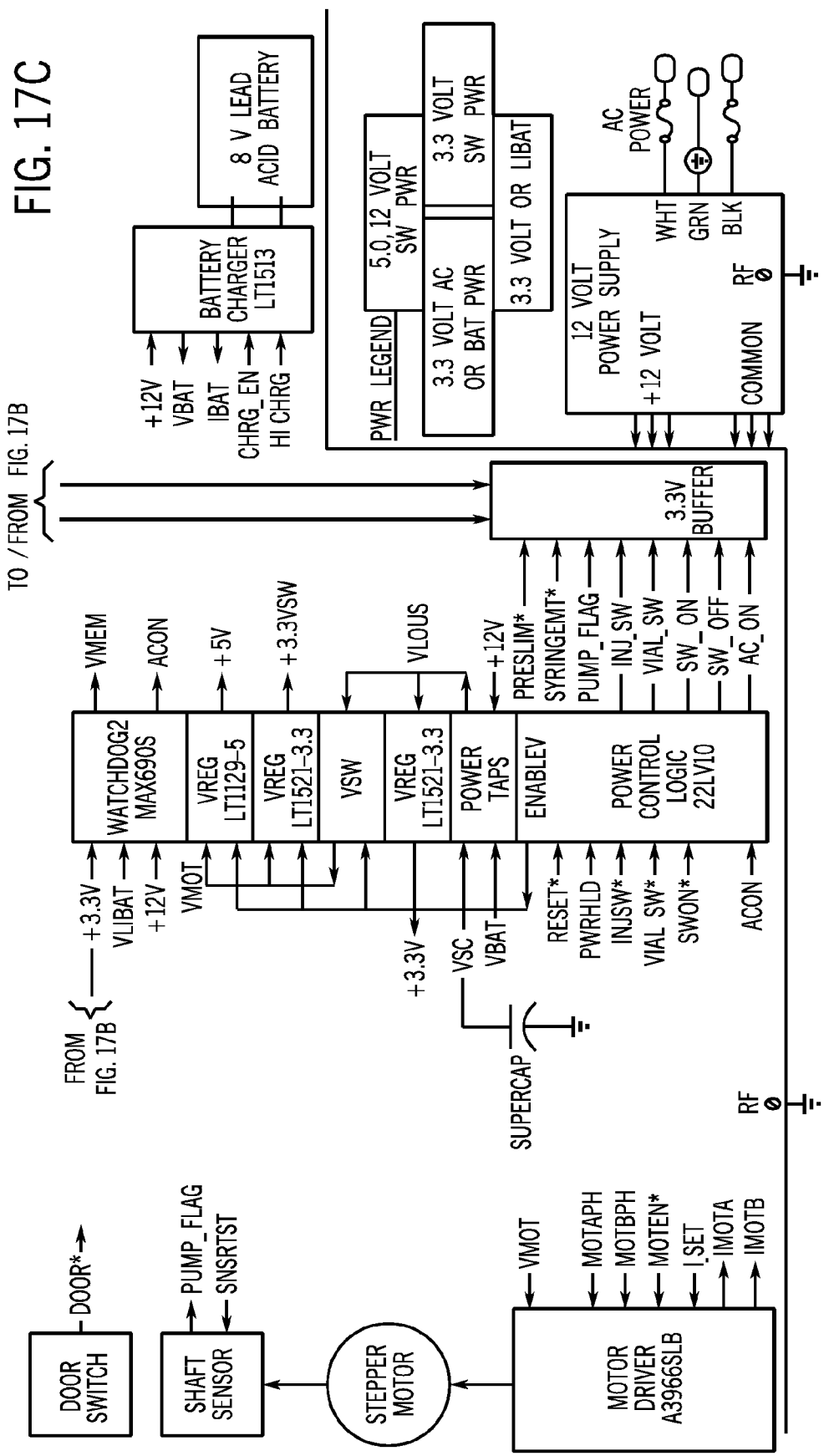
Figure 18:
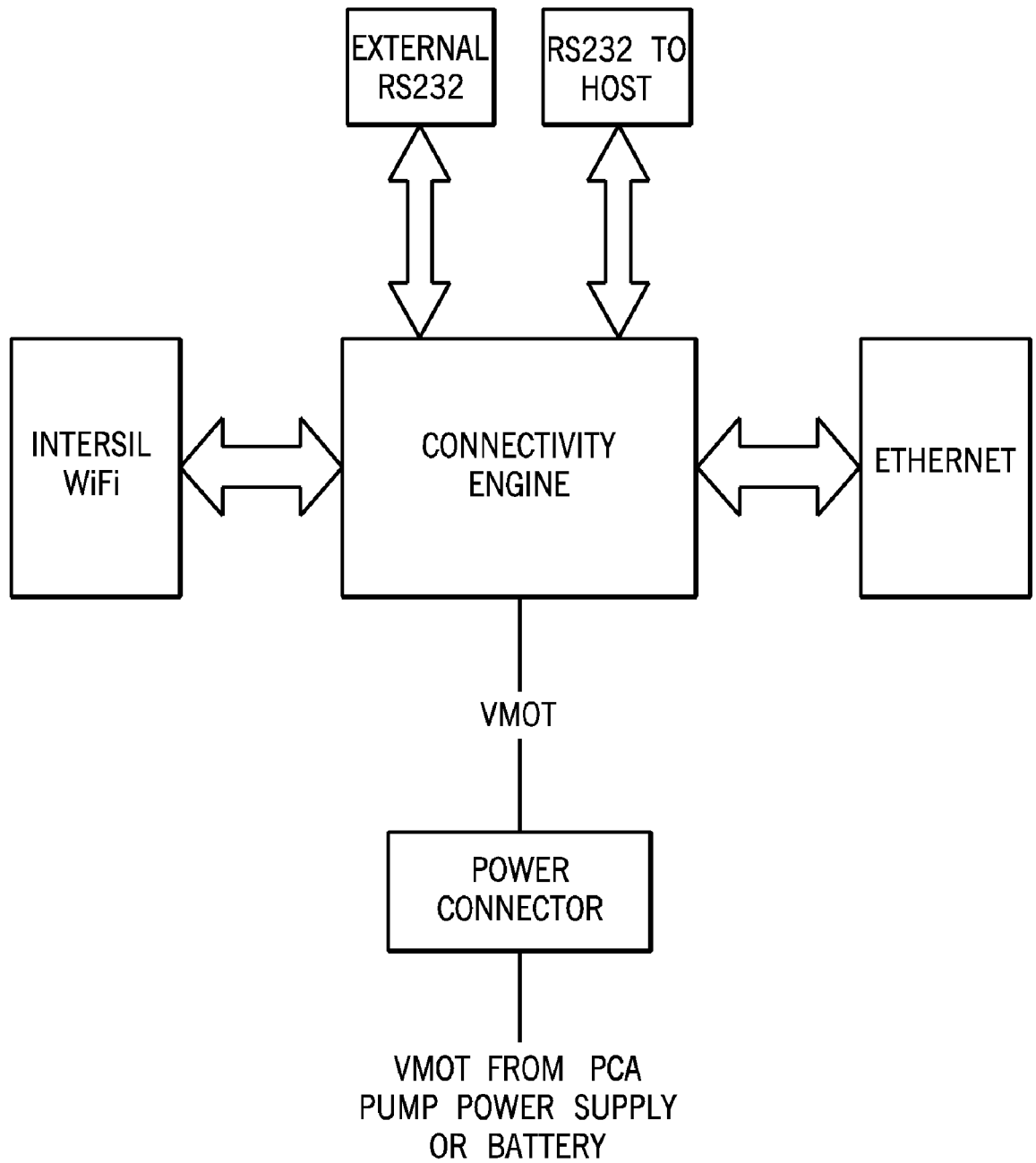
Figure 19:
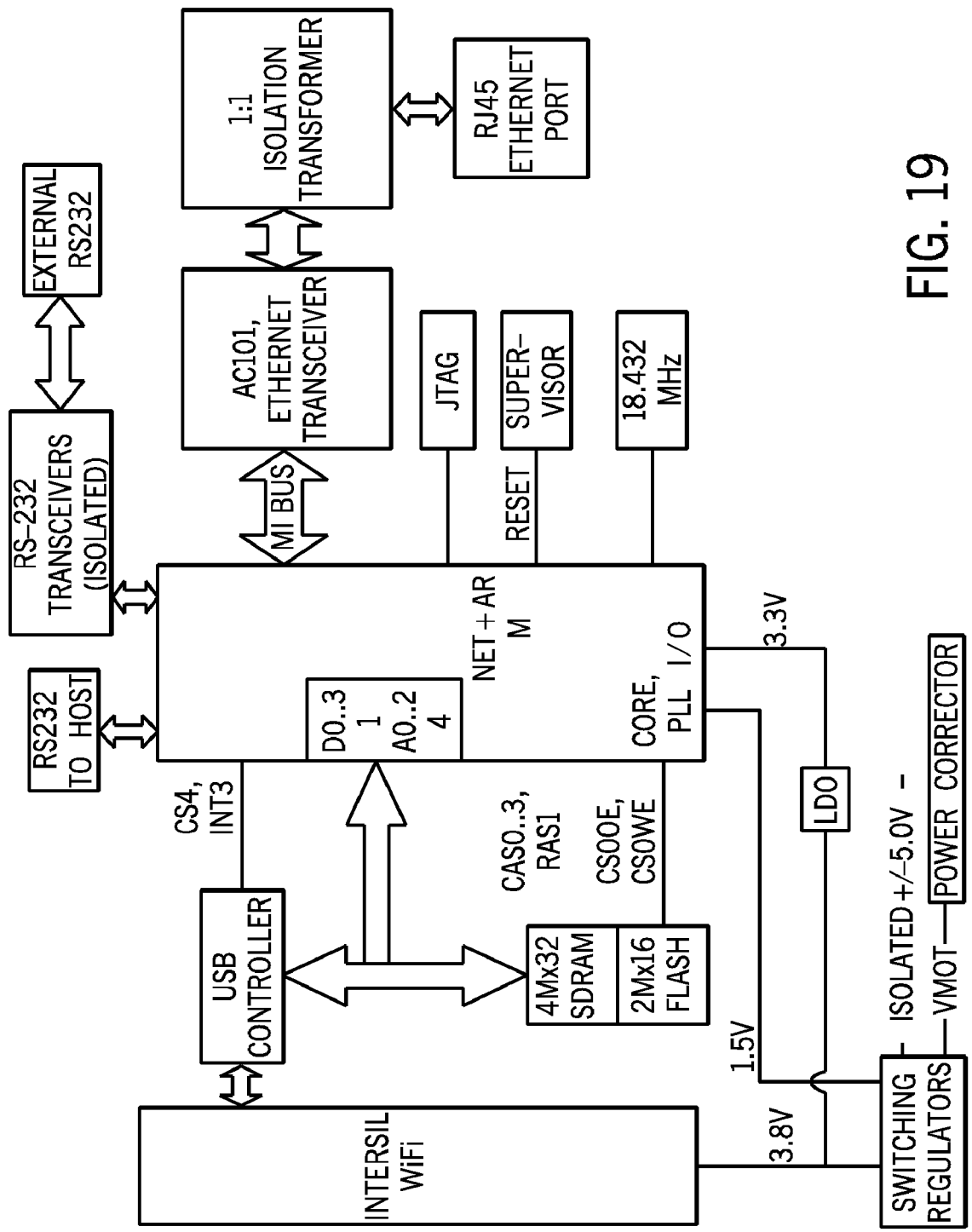

FIG. 17 is an electronic system block diagram of a patient-controlled analgesia (PCA) pump. FIGS. 18 and 19 are electronic system interface block diagrams of a connectivity engine that may be used with the PCA pump shown in FIG. 17. FIG. 17 includes a power supply, which supplies power to the system. A microcontroller interfaces with various components of the system, including a keypad, a patient pendent, serial port, bar code reader, various sensors, various switches, motor drivers, displays and LED indicators, and a speaker.

FIG. 18 is a block diagram of a connectivity engine that may be used with the PCA system shown in FIG. 17. FIG. 18 shows a connectivity engine and several interfaces including Ethernet, WiFi, an external RS232 serial interface, and an RS232 serial interface to the host device. FIG. 18 also illustrates that the connectivity engine can draw power (via a power connector) from the PCA pump (FIG. 17). The PCA pump generates a motor voltage VMOT for powering the various motors. The same voltage VMOT can be used to power the connectivity engine.

FIG. 19 is a more detailed block diagram of the connectivity engine of FIG. 18. The connectivity engine includes a connectivity engine controller (CEC), which is a wired/wireless connectivity module incorporating both a Ethernet processor and an 802.11b wireless transceiver. An Ethernet transceiver and all necessary circuitry to provides a 10/100 Base T interface through an RJ-45 jack. A USB controller and all the necessary circuitry controls a USB (host) interface with the WiFi. The two RS232 ports are connected to a system bus. The connectivity engine also includes FLASH and SDRAM memory.

In the preceding detailed description, the invention is described with reference to specific exemplary embodiments thereof. Various modifications and changes may be made thereto without departing from the broader scope of the invention as set forth in the claims. The specification and drawings are, accordingly, to be regarded in an illustrative rather than a restrictive sense.

What is claimed is:

1. A medical pump configuration and data logging system comprising:
   a host computer including a memory, a user interface and a display, the host computer being in communication via a communication network with at least one infusion pump to be configured for use in at least one of a plurality of clinical care areas within a medical facility;
   the memory storing a customizable drug library including infusion pump configuration information; and
   the user interface allowing a user to input an entry regarding infusion pump configuration information into a draft of the customizable drug library and save the draft of the customizable drug library as an active drug library in the memory for communication to the at least one infusion pump by the host computer via the communication network;

wherein the host computer applies an implied schema for validation in real time of the entry while the entry is being made by the user at the user interface such that the user is notified instantly on the display whenever the entry is invalid and is prevented from saving/adding an invalid entry to the draft of the customized drug library and thereby the active drug library;

wherein the implied schema is part of an Extensible Markup Language (XML) schema applied by the host computer, wherein the XML schema further includes an XML exchange schema that defines structure for data transfer between the host computer and the at least one infusion pump and the implied schema defines and validates values and types of data to be transferred such that infusion pump configuration information for different types of infusion pumps can be added to the active drug library and successfully communicated to the different types of infusion pumps.

2. The system of claim 1 wherein the different types of infusion pumps include infusion pumps having differing versions of pump software.

3. The system of claim 1 wherein the different types of infusion pumps include infusion pumps of different makes.

4. The system of claim 1 wherein the different types of infusion pumps include infusion pumps having different binary formats.

5. The system of claim 1 wherein the different types of infusion pumps include infusion pumps having different types of processors.

6. The system of claim 1 wherein the different types of infusion pumps include infusion pumps having differing numbers of infusion channels thereon.

* * * * *